(12) United States Patent
Carlen et al.

(10) Patent No.: US 6,251,942 B1
(45) Date of Patent: Jun. 26, 2001

(54) COMPOSITIONS AND METHODS FOR ALLEVIATING IMPAIRED MENTAL FUNCTION, MEMORY LOSS AND REDUCING RECOVERY TIME IN ANAESTHETIZED MAMMALS

(75) Inventors: Peter Louis Carlen, 529 St. Clements Avenue, Toronto, Ontario (CA), M5N 1M3; Christopher George Janus, Toronto; Hossam El-Beheiry, Mississauga, both of (CA)

(73) Assignee: Peter Louis Carlen, Toronto (CA)

( * ) Notice: Subject to any disclaimer, the term of this patent is extended or adjusted under 35 U.S.C. 154(b) by 0 days.

(21) Appl. No.: 09/316,203

(22) Filed: May 21, 1999

(30) Foreign Application Priority Data

May 26, 1998 (CA) .................................................. 2238548
Jun. 2, 1998 (CA) .................................................. 2239421

(51) Int. Cl.$^7$ ................................................. A61K 31/195
(52) U.S. Cl. .................................. 514/561; 424/DIG. 6; 514/534; 514/567; 514/568; 514/576; 514/601; 514/602; 514/716; 514/717; 514/718; 514/721; 514/741; 514/836
(58) Field of Search ...................... 424/DIG. 6; 514/601, 514/602, 716, 717, 718, 721, 741, 836, 534, 561, 567, 568, 576

(56) References Cited

U.S. PATENT DOCUMENTS

| | | | |
|---|---|---|---|
| 5,141,627 | * 8/1992 | Tsien et al. | 204/157.88 |
| 5,453,517 | * 9/1995 | Kuhn et al. | 549/227 |
| 6,015,834 | * 1/2000 | Charlton et al. | 514/561 |

FOREIGN PATENT DOCUMENTS

94/08573 * 4/1994 (WO) .

OTHER PUBLICATIONS

STN/CAS online, file LIFESCI, Acc. No. 1998:93593, (Spigelman et al., Neuroscience (1996), vol. 75, No. 2, pp. 559–572), Abstract.*
STN/CAS online, file LIFESCI, Acc. No. 96:45117, (Zhang et al., J. Neurophysiol. (1995), vol. 74, No. 6, pp. 2225–2241), Abstract.*
Ouanounou et al., Accumulation and extrusion of permeant Ca2+ chelators in attenuation of synaptic transmission at hippocampal CA1 neurons (Nov. 1996), Neuroscience, vol. 75, No. 1, pp. 99–109.*
Luo et al., 'Compromised mitochondrial function leads to increased cytosolic calcium and to activation of MAP kinases', Proc. Natl. Acad. Sci. USA (1997, Cell Biology), vol. 94, pp. 8705–9710.*
Ellis–Davies et al., 'Nitrophenyl–EGTA, a photolabile chelator that selectively binds Ca2+ with high affinity and releases it rapidly upon photolysis', Proc. Natl. Acad. Sci. USA (1994, Physiology), vol. 91, pp. 187–191.*
Ghasemi et al., 'A kinetic study of complex formation between calcium ion and cryptand C221 in dimethylsulphoxide solution', Polyhedron (1996), vol. 15, pp. 923–927.*

* cited by examiner

*Primary Examiner*—Jose' G. Dees
*Assistant Examiner*—Frank Choi
(74) *Attorney, Agent, or Firm*—Jeffrey S. Melcher; Manelli, Denison & Selter, PLLC

(57) ABSTRACT

Composition and methods of alleviating impaired mental function and memory loss in mammals and reducing the recovery time from anaesthesia in age mammals, comprising treating the mammal with a non-toxic, enhancing effective amount of a cell membrane permeant calcium buffer. The buffer is preferably a calcium ion chelating agent having a $K_D$ selected from the range $1\times10^{-4}$ to $1\times10^{-8}$ Molar and being essentially calcium ion-selective over other metal ions. A most preferred buffer is BAPTA-AM.

12 Claims, 7 Drawing Sheets

COMPOSITIONS AND METHODS FOR ALLEVIATING IMPAIRED MENTAL FUNCTION, MEMORY LOSS AND REDUCING RECOVERY TIME IN ANAESTHETIZED MAMMALS

FIELD OF THE INVENTION

This invention relates to methods of alleviating impaired mental function, memory loss and reducing recovery time in anaesthetized mammals using a cell membrane permeant calcium buffer, said calcium buffers per se, pharmaceutical compositions comprising said calcium buffers and methods for the preparation of said pharmaceutical compositions.

BACKGROUND OF THE INVENTION

Progressive learning and memory impairment occurs during the normal course of aging (1,2,3). A strong functional link has been established between the hippocampal region of the brain and learning and memory of spatial information (4,5,6). Also, age-related changes in neuroanatomical, neurochemical and neurophysiological parameters of this structure of the brain have been well documented and causally linked to the etiology of memory impairment (5,7,8). This age-dependent impairment of spatial learning is strongly correlated with a deficit in the maintenance of neuronal activity long-term potentiation (LTP) in the hippocampus (9). LTP, a form of synaptic plasticity, is postulated as a molecular substrate of spatial learning (4,10,11). The functioning of neurons and synaptic activity are heavily dependent on calcium ions ($Ca^{2+}$). For example, calcium is involved in LTP (10), in the regulation of membrane excitability (12) and serves directly as a second and third messenger in neurons (13,14). Moreover, several lines of evidence from rodent species point to the hypothesis that changes in the neuronal calcium homeostasis coincide with aging of the brain in general, and may be correlated with age-related decline in cognitive functions (15,16,17). For example, hippocampal calcium channels increase their activity in aged brain (18) and the density of L-type calcium channels is increased in aged hippocampal CA1 neurons (19). The experimental evidence has led to the suggestion that changed calcium homeostasis in aged neurons may be a contributing factor to some memory deficits caused by aging (20,21,22).

High voltage activated calcium currents were enhanced in dentate granule neurons from aged rats by EGTA introduced intracellulary in the recording electrode (23). Also, reduced field Excitatory Postsynaptic Potential (fEPSP) in the hippocampal slices of old rats relative to that observed in the younger age groups was found to be correlated with impaired spatial learning in aged animals (24,25). Further evidence supporting the hypothesis that a calcium increase in aged neurons may be implicated in memory impairment comes from in vivo studies on the role of the calcium channel blocker, nimodipine. This drug reduced the number of age-related motor impairments in aged rats (26), and enhanced their recent memory (27).

The elderly are known to exhibit an increased incidence of post-operative confusional states including post-anaesthetic delirium due to aging-enhanced sensitivity to anaesthetic agents.

An inverse relationship between age and inhaled anaesthetic requirements has been observed in both humans and experimental animals (39,40). The mechanisms underlying the age dependency of inhalational anaesthetic potencies may arise from direct changes in target tissue responsiveness (41) or from pharmacokinetic changes, i.e. drug disposition, metabolism and elimination. Previous reports failed to elucidate significant age-related changes in blood solubilities of volatile agents or in their equilibration kinetics with brain tissue during anaesthesia (42,43). Ageing, however, is associated with alterations in neuronal morphology and density (44), metabolism (45) and neurotransmitter activities (46). Accordingly, the age-dependent decrease in anaesthetic requirement is probably due to increased vulnerability of specific sites in the central nervous system to anaesthetic action.

It has been reported that ageing potentiates anaesthetic-induced synaptic depression in hippocampal slices (47). In this study (47), the effects of the volatile anaesthetic, isoflurane, on dendritic field excitatory postsynaptic potentials (fEPSP) were compared in hippocampal slices taken from young mature and old Fisher 344 rats. Application of isoflurane (1% v/v) to young brain slices produced minimal effects on the recorded fEPSPs. On the contrary, the same anaesthetic concentration depressed field responses obtained from old hippocampal slices by 42+6.8% compared with baseline values. Such increased sensitivity to anaesthetic action in the old slices was consistently observed with administration of higher isoflurane concentrations. The presynaptic afferent volley was unaffected by application of low or high anaesthetic concentration, suggesting that age-induced changes in nerve fibre conduction and probably nerve ending excitability are not involved in the increased vulnerability of old synapses to anaesthetic action. It was concluded that other synaptic sites are probably involved in the mechanisms of age-dependent potentiation of anaesthetic suppression of synaptic transmission. It has been reported (48,49) that aging-induced potentiation of anaesthetic actions on synaptic transmission could be opposed by maneuvers that decreases $[Ca^{2+}]_i$.

Australian Patent No. 677,613, published May 9, 1994—Charlton et al discloses a method of reducing the damaging effect of an injury to mammalian cells by treatment of the cell or mammalian tissue in vivo with a cell membrane permeant calcium buffer. The method comprises treating mammalian tissue with a damage reducing effective amount of the calcium buffer, preferably, a BAPTA derivative. The method may be used to control the concentration of $Ca^{2+}$ ions in the vicinity of ion channel pores of the cells to prevent diffusion of toxic amounts of $Ca^{2+}$ ions to subcellular sites located near the source of $Ca^{2+}$ influx. The buffer treatment may be applied as a prophylactic or after the mammalian tissue has sustained injury. Pharmaceutical compositions comprising the calcium buffer and method of manufacture therefor are described.

A water maze test (28) for the evaluation of spatial learning of aged rats has been widely used in neurobiological studies of hippocampal function and in the characterization of cognitive deficits in the aged rats (7,25,29,30).

In vitro studies of BAPTA-AM and EGTA-AM with hippocampal slices from young and mature rats using extra cellular field recordings from the stratum radiatum of the CA1 region showed depression of the amplitude of field excitatory post synaptic potentials (fEPSP) of up to 60% in the younger slices but enhanced the fEPSP of the perfused aged slices by 30% (38).

PUBLICATIONS

1. Barnes, C. A. (1990). Animal models of age-related cognitive decline. In F. Boller, & J. Grafman (Eds.), *Handbook of neuropsychology*. Amsterdam, The Netherlands: Elsevier Science Publishers.

2. Craik, F. I. M., Anderson, N. D., Kerr, S. A., & Li, K. Z. H. (1995). Memory changes in normal aging. In A. D. Baddeley, B. A. Wilson, & F. N. Watts (Eds.), *Handbook of memory disorders* (pp. 211–241). New York, N.Y.: Willey.
3. De Toledo-Morrel, L., Geinisman, Y., & Morrell, F. (1988). Age-dependent alterations in hippocampal synaptic plasticity; Relation to memory disorders. Neurobiology of Aging, 9, 581–590.
4. Morris, R. G. M. (1990). *Toward a representational hypothesis of the role of hippocampal synaptic plasticity in spatial and other forms of learning*: Cold Spring Harbour Laboratory Press.
5. Morris, R. G. M., Garrund, P., Rawlings, J., & O'Keefe, J. (1982). Place navigation impaired in rats with hippocampal lesions. *Nature*, 297, 681–683.
6. Squire, L. R. (1992). Memory and the hippocampus: a synthesis from findings with rats, monkeys, and humans. *Psychological Review*, 99, 195–231.
7. Gallagher, M., & Nicolle, M. M. (1993). Animal-models of normal aging—relationship between cognitive decline and markers in hippocampal circuitry. *Behavioural Brain Research*, 57, 155–162.
8. O'Keefe, J., & Nadel, L. (1978). *The Hippocampus as a Cognitive Map*. Oxford: Oxford University Press.
9. Bliss, T. V. P., & Lomo, T. (1973). Long-lasting potentiation of synaptic transmission in the dentate area of the unanaesthetised rabbit following stimulation of perforant path. *Journal of Physiology*, 232, 357–374.
10. Bliss, T. V. P., & Collingridge, G. L. (1993). A synaptic model of memory: long-term potentiation in the hippocampus. *Nature*, 361, 31–39.
11. Eichenbaum, H. (1996). Learning from LTP: a comment on recent attempts to identify cellular and molecular mechanisms of memory. *Learning & Memory*, 3, 61–73.
12. Tsien, R. Y. (1980). New calcium indicators and buffers with high selectivity against Mg and protons: design, synthesis, and prototype structures. *Biochemistry*, 19.
13. Augustine, G. J., Charlton, M. P., & Smith, S. J. (1985). Calcium entry and transmitter release at voltage-clamped terminals of squid. *Journal of Physiology*, 367, 167–181.
14. Gosh, A., & Greenberg, M. E. (1995). Calcium signaling in neurons: molecular mechanisms and cellular consequences. *Science*, 268, 239–247.
15. Gibson, G. E., & Peterson, C. (1987). Calcium and the aging nervous system. *Neurobiology of Aging*, 8, 329–344.
16. Iacopino, A. M., & Christakos, S. (1990). Specific reduction of calcium binding protein (28-kilodalton calbindin-D) gene expression in aging and neurodegenerative desease. *Proceedings of the National Academy of Sciences U.S.A.*, 87, 4078–4082.
17. Michaelis, M. L., Johe, K., & Kitos, T. E. (1984). Age-dependent alterations in synaptic membrane systems for calcium regulation. *Mec Aging Development*, 25, 215–225.
18. Landfield, P. W. (1994). Increased hippocampal Ca2+ channel activity in brain aging and dementia. *Annales of NY Academy of Sciences*, 747, 351–364.
19. Thibault, O., & Landfield, P. W. (1996). Increase in single L-type calcium channels in hippocampal neurons during aging. *Science*, 272, 1017–1020.
20. Khachaturian, Z. C. (1989). The role of calcium regulation in brain aging: reexamination of a hypothesis. *Aging*, 1, 17–34.
21. Khachaturian, Z. C. (1994),. Calcium hypothesis of Alzheimer's disease and brain aging. *Annales of NY Academy of Sciences*, 747, 1–11.
22. Khachaturian, Z. S., Cotman, C. W., & Pettegrew, J. W. (1989). *Calcium, membranes, aging, and Alzheimer's disease*. New York: The New York Academy of Sciences.
23. Reynolds, J. N., & Carlen, P. L. (1989). Diminished calcium currents in aged hippocampal dentate gyrus granule neurons. *Brain Research*, 479, 384–390.
24. Barnes, C. A., Rao, G., Foster, T. C., & McNaughton, B. L. (1992). Region-specific age effects on AMPA sensitivity: electrophysiological evidence for loss of synaptic contacts in hippocampal field CA1, *Hippocampus*, 2, 457–468.
25. Barnes, C. A., Rao, G., & McNaughton, B. L. (1996). Functional integrity of NMDA-dependent LTP induction mechanisms across the lifespan of F-344 rats. *Learning & Memory*, 3, 124–137.
26. Schuurman, T., & Traber, J. (1989). Old rats as an animal model for senile dementia: behavioural effects of nimodipine. In M. Bergener, & B. Reisberg (Eds.), *Diagnosis and treatment of senile dementia*. Berlin: Springler-Verlag.
27. Levere, T. E., & Walker, A. (1991). Old age and cognition: enhancement of recent memory in aged rats by calcium channel blocker nimodipine. *Neurobiology of Aging*, 13, 63066.
28. Morris, R. G. M. (1981). Spatial localization does not require the presence of local cues. *Learning & Motivation*, 12, 239–260.
29. Fisher, W., Chen, K. S., Gage, F. H., & Bjurklund, A. (1991). Progressive decline in spatial learning and integrity of forebrain cholinergic neurons in rats during aging. *Neurobiology of Aging*. 13, 9–23.
30. Markowska, A. L., Long, J. M., Johnson, C. T., & Olton, D. S. (1993). Variable-interval probe test as a tool for repeated measurements of spatial memory in the water maze. *Behavioral Neuroscience*, 107, 627–632.
31. Shionori, H. (1993). Pharmacokinetic drug interactions with ACE inhibitors. *Clinical Pharmacokinetics*, 25, 20–58.
32. Cain, D. P., Saucier, D., Hall, J., Hargreaves, E. L., & Boon, F. (1996). Detailed behavioral analysis of water maze acquisition under APV or CNQX: contribution of sensorimotor disturbances to drug-induced acquisition deficits. *Behavioral Neuroscience*, 110, 86–102.
33. Saucier, D., L., H. E., Boon, F., Vanderwolf, C. H., & Cain, D. P. (1996). Detailed behavioural analysis of water maze acquisition under systemic NMDA or muscarinic antagonism: nonspatial pretraining eliminates spatial learning deficits. *Behavioral Neuroscience*, 110, 103–116.
34. Gallagher, M., Burwell, R., & Burchinal, M. (1993) Severity of spatial learning impairment in aging: development of leaning index for performance in the Morris water maze. *Behavioral Neuroscience*, 107, 618–626.
35. Morris, R. G. M. (1989). Synaptic plasticity and learning: selective impairment of leaning in rats and blockade of long-term potentiation in vivo by the N-methyl-D-asparate receptor antagonist AP5. *Journal of Neuroscience*, 9, 3040–3057.
36. Wehner, J. M., Sleight, S., & Upchurch, M. (1990). Hippocampal protein kinase C activity is reduced in poor spatial learners. *Brain Research*, 523, 181–187.
37. Stevens, J. (1990). *Intermediate statistics: a modern approach*. Hillsdale, New Jersey: Lawrence Erlbaum Associates, Inc., Publishers.
38. Ouanounou A., Zhang L., Charlton M. P. and Carlen P. L.—Excitatory Synaptic Transmission is Enhanced in Aged Hippocampal Synaptic. CAI Neurons by Calcium Chelators. Experimental Biology, 1996.

39. White P. F., Richard R. J. and Eger E. I. *Anesthesiology*, 40, 52–57, (1974).
40. Stevens W. C., Dolan W. M., Gibbons R. T. et al. *Anesthesiology*, 42, 197–200, (1975).
41. Franks N. P. and Lieb W. R. *Nature*, 367, 607–614 (1994).
42. Chortkoff B. S., Laster M. J., Koblin D. D. et al. *Anesthesia Analgesia*, 79, 234–237, (1994).
43. Strum D. P., Eger E. I II, Unadkat J. D. et al. *Anesthesia Analgesia*, 73, 310–318, (1990).
44. Geinsman C. M., Bondareff W. and Doge W. T. *Am. J. anat.* 152, 321–330, (1978).
45. Smith B. E. *Trends Neurosci* 7, 203–208, (1984).
46. Basyks A., Reynolds J. N. and Carlen P. L. *Brain Res.* 530, 142–146, (1990).
47. El-Beheiry H., Ouanouvou A. and Carlen P. L. Ageing potentiates anaesthetic induced synaptic depression in hippocampal slices. *NeuroReport*, 7, 502–504, (1996).
48. El-Beheiry H., Ouanounou A. and Carlen P. L. (1998) Low extracellular calcium opposes isoflurane actions in aged neurons. *Br. J. Anaesth.* 80 (S 1):104.
49. Ouanounou A., Carlen P. L. and El-Beheiry H. (1998). Effects of isoflurane on excitatory synaptic transmission in old hippocampal formation. *Br. J. Pharmacol.* (in press).
50. Miu P. and Puil E. (1989). Isoflurane-induced impairment of synaptic transmission in hippocampal neurones. *Exp. Brain Res.* 75:354–360.
51. White P. F., Johnston R. R. and Eger E. I. II (1974). Determination of anaesthetic requirement in rats. *Anesthesiology* 40:52–57.
52. Eger E. I. II, Saidman L. J. and Brandstater B. (1965). Minimum alveolar concentration: a standard of anesthetic potency. *Anesthesiology* 26:756–763.

SUMMARY OF INVENTION

As a result of extensive investigations, we have discovered a method of alleviating impaired mental function and, particularly cognitively impaired mental function and memory loss in mammals.

We have also found that vulnerability to anaesthesia is partially antagonized by treatment with a cell membrane permeant calcium buffer to effect reversing aging potentiation of anaesthetic actions and to decrease the incidence of post-operative adverse events and clinically significant complications in elderly mammals, including human beings. We have found that aforesaid calcium buffers effect enhancement of anaesthetic requirements and a decrease in recovery time from anaesthesia.

It is an object of the present invention to provide methods of alleviating impaired mental function, particularly cognitively impaired mental function, memory loss and reducing recovery time in anaesthetized mammals, particularly aged mammals.

It is a further object to provide pharmaceutical compositions for use in said treatments of said mammals in vivo to alleviate impaired mental function, memory loss and reducing recovery time in anaesthetized mammals.

The present invention in one aspect is based on the discovery of the role of cell membrane permeant calcium buffers in elevating some aspects of memory dysfunction caused by senescense in aged mammals.

The dysfunction in calcium homeostasis in brain neurons is thought to be one of the contributing factors to cognitive dysfunction in senescent humans and animals Aged rats show impairment in their cognitive abilities and increased calcium level in the specific hippocampus and cortex regions of their brain. We have found that in vivo treatment with the cell permeant calcium buffer, bis (O-aminophenoxy)-ethane-N,N,N,N-tetraacetic acid—acetoxymethyl ester (BAPTA-AM) affected the spatial memory of rats. Aged (22 months old) Fisher 344 rats were trained in a hidden platform version of a water maze constituting a hippocampally dependent learning task. The results showed that: (a) adminstration of BAPTA-AM (5 mg/kg) before each training session significantly improved rats' performance in the water maze; b) the improvement was mostly visible within the first 4–5 days of 8 days training; (c) all rats showed comparable performance at the end of training, but the controls never achieved better scores than BAPTA rats; and (d) a retention test carried out 35 days after the last BAPTA-AM injection revealed long lasting tendency of positive effect of the drug on the rats' spatial memory without affecting their locomotor behaviour.

Without being bound by theory, we believe that the present invention relates to the consequences of increased levels of intracellular calcium during aging. We have found that BAPTA-AM ameliorated dysfunction on learning and memory of synaptic transmission caused by chronically raised $Ca^{++}$ levels in aged brain slices. Decreasing intracellular free $Ca^{++}$ levels in the brain of aged mammals enhanced this spatial learning and the retention of spatial information. The retention tests indicated a long lasting positive trend on the rats' spatial ability.

Accordingly, the invention in one aspect provides alleviating impaired mental function in mammals by treating the mammal with a non-toxic, enhancing effective amount of a cell membrane permeant calcium buffer.

Accordingly, in a further aspect the invention provides a method of reducing the recovery time from anaesthesia for an aged mammal, said method comprising treating said mammal under said anaesthesia with a non-toxic, effective amount of a cell membrane permeant calcium buffer.

By the term "recovery from anaesthesia" in this specification, is meant recovery from post-anaesthesia confusion such that the mammal comes out of the coma, and re-affirms its ability to stand, attain balance and possess dexterity.

The buffer is, preferably, present in an amount to reduce or maintain intracellular calcium ion concentration to below millimolar levels.

Preferably, the cell membrane permeant buffer is a calcium ion chelating agent and more preferably a buffer having a $K_D$ selected from the range $1\times10^{-4}$ to $1\times10^{-8}$ Molar. Yet more preferably, the buffer is essentially calcium selective over other metal ions to provide minimal disruption to other metal e.g. Fe, Mg, K, Na, ion balances in the cell.

By the term $K_D$ is meant the ratio of the forward and reverse rate constants of the dissociation of the buffer—calcium salt (BCa) to buffer (B) and $Ca^{2+}$ ions as represented by the general equation $$BCa \underset{K_2}{\overset{K_1}{\rightleftharpoons}} B + Ca^{2+}; K_D = \frac{K_1}{K_2}$$

To effectively protect mammalian cells against impaired mental function, preferably, the effective amounts of $Ca^{2+}$ buffer inside the cell should be in the concentration range of 10 $\mu$M to 10 mM. This keeps intracellular calcium concentrations from rising to millimolar levels In a first form, the preferred compounds of use in the practice of the invention are comprised of a BAPTA-like chelator, in which the two halves of the chelator are linked by a linkage selected from the group comprised of: (a) a simple 1,2-ethanediyl (—Ch$_2$CH$_2$—) moiety having bulky substituents such as —CH$_3$, —C$_2$H$_5$, or —CH$_3$OH added thereto; (b) a 1,2-ethanediyl moiety incorporated into a carbocyclic ring; and (c) a 1,2-ethanedlyl moiety incorporated into a carbocyclic ring; wherein the chelator is coupled to a single 2-nitrobenzyl derivative, which in turn is a photochemical precursor of a 2-nitrosobenzophenone. In this form the new compounds are preferably comprised of a chemical compound having the generic formula;

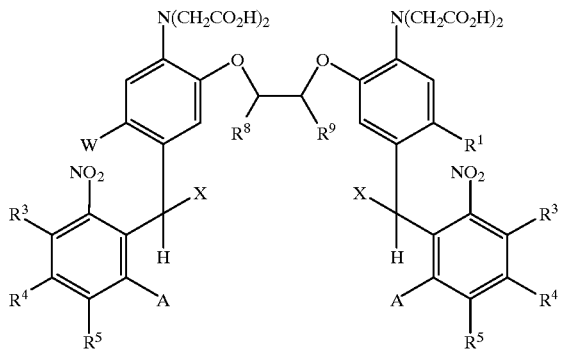

and the pharmaceutically acceptable nontoxic salts and esters thereof wherein;

A is —NO$_2$ or —H;

R$^1$ is selected from the group comprised of H, CH$_3$, FCl, and Br;

R$^3$, R$^4$ and R$^5$ are independently H, OH, NR$^6$R$^7$, or alkoxy, or

R$^3$ and R$^4$ together are —OCH$_2$O— or —OCH$_2$CH$_2$O— and R$^5$ is H, OH, NR$^6$R$^7$, or alkoxy, or R$^4$ and R$^5$ together are —OCH$_2$O— or —OCH$_2$CH$_2$O— and R$^3$ is H, OH, NR$^6$R$^7$ or alkoxy;

X is selected from the group comprised of OH, alkoxy, Cl, Br, NR$^6$R$^7$, —OCOCH$_3$, —OCOCF$_3$, —OCOCH$_2$NH$_2$, —OPO$_3$H, and —OSO$_2$CH$_3$;

R$^6$ and R$^7$ are independently H, methyl or ethyl;

R$^8$ and R$^9$ are independently H, CH$_3$, C$_2$H$_5$ or CH$_2$OH except that both may not be —H simultaneously; or R$^8$ and R$^9$ together are —(CH$_2$)$_m$—Y—(HK$_2$)$_n$— where m and n are independently 1 or 2 and Y is selected from the group comprised of —CH$_2$—, —O—, —NR$^6$, —S—, and —S—S; and W is H, OH, or —NHR$^6$.

In a second form, the compounds are preferably comprised of a BAPTA-like chelator, in which the two halves of the chelator are linked by a linkage selected from the group comprised of: (a) a simple 1,2-ethanediyl (—CH$_2$CH$_2$) moiety having bulky substituents such as CH$_3$, C$_2$H$_5$ or —CH$_2$OH added thereto; (b) a 1,2-ethanediyl moiety incorporated into a carbocyclic ring; and (c) a 1,2-nitrobenzyl derivatives, themselves photochemical precursors of the related 2-nitrosobenzophenones. In this form, the compounds are preferably comprised of a chemical compound having the generic

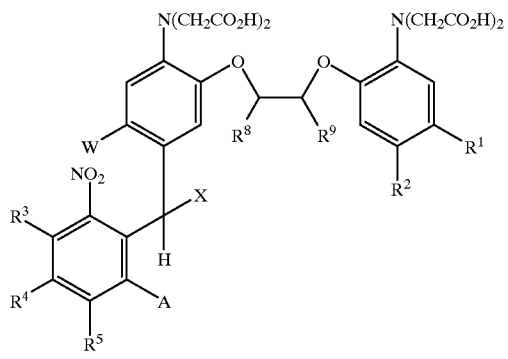

and the pharmaceutically acceptable non-toxic salts and esters thereof wherein:

A is NO$_2$ or H;

R$^1$ is selected from the group comprised of H (unless R$^2$ is also H), CH$_3$, F, Cl, and Br;

R$^2$ is selected from the group comprised of H (unless R$^1$ is also H), CH$_3$, F, Cl, and Br; and C$_1$–C$_4$ alkoxy;

R$^3$, R$^4$ and R$^5$ are independently H, OH, NR$^6$R$^7$, or alkoxy, or

R$^3$ and R$^4$ together are —OCH$_2$O— or —OCH$_2$CH$_2$O— and R$^5$ is H, OH, NR$^6$R$^7$ or alkoxy, or R$^4$ and R$^5$ together are —OCH$_2$O— or —OCH$_2$CH$_2$O— and R$^3$ is H, OH, NR$^6$R$^7$ or alkoxy;

X is selected from the group comprised of OH, alkoxy, Cl, Br, NR$^6$R$^7$, —OCOCH$_3$, —OCOCF$_3$, —OCOCH$_2$NH$_2$, —OPO$_3$H, and —OSO$_2$CH$_3$;

R$^6$ and R$^7$ are independently H, methyl or ethyl;

R$^8$ and R$^9$ are independently H, CH$_3$, C$_2$H$_5$, or CH$_2$OH except that both may not be H simultaneously; or R$^8$ and R$^9$ together are —(CH$_2$)$_m$—Y—(CH$_2$)$_n$— where m and n are independently 1 or 2 and Y is selected from the group comprised of —CH$_2$—, —O—, —NR$^6$, —S—, and —S—S—; and W is H, OH, or NHR$^6$.

In a third form, the preferred compounds of use in the practise of the invention fall within the general formula:

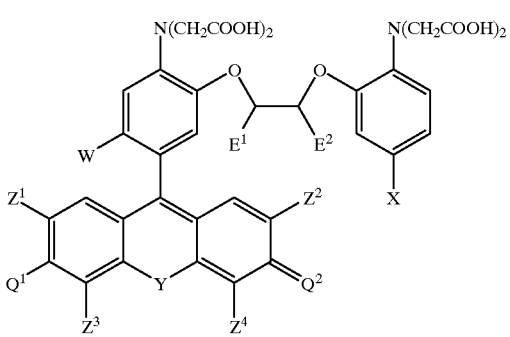

and the pharmaceutically acceptable non-toxic salts and esters thereof wherein:

E$^1$ and E$^2$ are independently H, CH$_3$, C$_2$H$_5$, CH$_2$OH, COOH or CH$_2$COOH or E$^1$ and E$^2$ together are —(CH$_2$)$_m$—V—(CH$_2$)$_n$— where m and n are independently 1 or 2 and V is selected from the group consisting of —CH$_2$—, —O—, NH—, —NMe—, —S—, and —S—S—;

W is H, OH, or COOH;

X is H, Me, COOH, F, Cl, Br, I or $NO_2$;

Y is —O—, —NMe—, —S—, —$CH_2$—, —$CMe_2$—, —$CF_2$—, or a direct sigma bond making a five-membered central ring;

$Z^1$, $Z^2$, $Z^3$ and $Z^4$ are independently H, F, Cl, Br, I, or Me, and $Q^1$, $Q^2$ equal $R_1$, $R_2$ N—, or HO—, O=, where $R^1$ and $R^2$ are independently selected from the group consisting of H, Me, and Et; or $Z^1$, $Q^1$ or $Z^3$, together are —$(CH_2)_3$—N—$(CH_2)_3$ and $Z^2$, $Q^2$, $Z^4$ together are —$(CH_2)_3$—N—$(CH_2)_3$—.

Preferably, the tetraacetic acid esters are alpha-acyloxyalkyl esters, and more preferably, the alpha-acyloxyalky esters are acetoxymethyl esters.

In a fourth form, the chemical compound preferably has the general formula:

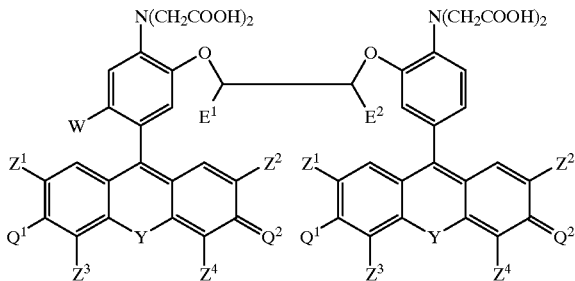

and the pharmaceutically acceptable non-toxic salts and esters thereof wherein:

$E^1$ and $E^2$ are independently H, $CH_3$, $C_2H_5$, $CH_2OH$, COOH, or $CH_2COOH$, or $E^1$ and $E^2$ together are —$(CH_2)_m$—V—$(CH_2)_n$— where m and n are independently 1 or 2 and V is selected from the group consisting of —$CH_2$—, —O—, NH—, —NMe—, —S—, and —S—S—; W is H, OH, or COOH;

Y is —O—, —NMe—, —S—, —$CH_2$—, —$CMe_2$—, —$CF_2$—, —CO— or a direct sigma bond making a five-membered central ring;

$Z^1$, $Z^2$, $Z^3$ and $Z^4$ are independently H, F, Cl, Br, I or Me, and $Q^1$, $Q^2$ equal $R_1R_2N$—, or HO—, O= or $R_1R_2N$—, O—, where $R^1$ and $R^2$ are independently selected from the group consisting of H, Me, and Et; or $Z^1$, $Q^1$, or $Z^3$ together are —$(CH_2)_3$—N—$(CH_2)_3$ and $Z^2$, $Q^2$, $Z^4$ together are —$(CH_2)_3$—N—$(CH_2)_3$—.

In a fifth form, a preferred chemical of use in the practise of the invention is a compound of the formula:

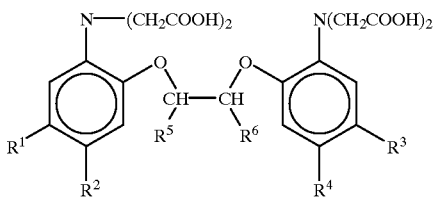

and the salts or the non-polymeric esters thereof wherein $R^1$ and $R^3$ are each independently selected from H, OH, $CH_3$, F, Cl, Br, I, —COOH, CN, $NO_2$ or —$NHR^7$ wherein $R^7$, is independently selected from H, methyl or ethyl;

$R^2$ is —(C=O)$CR^8$—N—N, wherein $R^8$ is independently selected from H, $C_1$–$C_4$ alkyl, phenyl, —COOH, —$COOR^7$ —(C—O)$CH_3$, or $CF_3$ wherein $R^7$ is as hereinbefore defined.

$R^4$ is independently selected from $R^2$, H, $CH_3$, $CH_2CH_3$, F, Cl, Br, I, COOH, CN or $NO_2$;

$R^5$ and $R^6$ are each independently selected from H, $CH_3$, $CH_2CH_3$, phenyl, or —$CH_2OH$, or $R^5$ and $R^6$ together form —$(CH_2)_m$—Y—$(CH_2)_n$— where m and n are each independently 1 or 2, and Y is selected from —$CH_2$—, —O—, —$NHR^7$, —S— or —S—S—S, and wherein $R^7$ is as defined hereinabove.

DEFINITIONS

In the present specification and claims, reference will be made to phrases and terms of art which are expressly defined for use herein as follows:

As used herein, "[$Ca^{2+}$]i" means intracellular free calcium.

As used herein, "EGTA" means ethylene glycol bis(-beta-aminoethyl ether-) N,N,N'N'tetraacetic acid.

As used herein, "BAPTA" means 1,2-bis(2-aminophenoxy)ethane N,N,N',N'-tetraacetic acid.

As used herein, "quin-2" mans 2-[[2-bis(carboxymethyl)amino]-5-methylphenoxy]-6-methoxy-8-bis(carboxymethyl)amino]quinoline.

As used herein, "BAPTA-like" means substituted derivatives of BAPTA which retain the essential characteristic of two bis (carboxymethyl) amino-substituted phenyl rings, said rings being linked at the positions ortho to the amines through a four atom bridge wherein the atom adjacent to each phenyl ring is N or O and the two center atoms are each C. By this definition, it is means that "BAPTA-like" includes compounds like quin-1 and quin-2.

As used herein, pharmaceutically acceptable esters mean those readily hydrolyzable esters which are known and used in the pharmaceutical industry, especially alpha-acyloxyalkyl esters.

As used herein pharmaceutically acceptable non-toxic salts mean carboxylic acid salts, wherein the counterion or ions are all Na, K, $NR_4^+$ (where R=H, $C_1$–$C_4$ alkyl or a mixture thereof), choline, N-methyl-glucamine, Ca, or Mg, or some combination of these counterions, or some combination of acid salts or these counterions plus free acid groups.

By the term "cell membrane permeant calcium buffer" is meant a calcium ion chelating agent which per se is membrane permeant or a membrane permeant derivative thereof which releases the calcium ion chelating agent within the cell, for example ester, amide and other suitable derivatives which release the chelating agent per se, and pharmaceutically acceptable non-toxic salts thereof.

Examples of most preferred calcium buffers of use in the practise of the invention are those known in the art as follows:

BAPTA-AM (1,2-bis (2-aminophenoxy) ethan—N,N,$N^1N^1$-tetraacetic acid—acetoxymethyl ester;

EGTA-AM (ethyleneglycol bis 2-aminoethyl ether) N,N,$N^1N^1$-tetraacetic acid acetoxymethyl ester;

5,5 dibromo BAPTA-AM 5,5-difluoro BAPTA-AM 4,4-difluoro BAPTA-AM

By the term "aged" in regards to mammals, rats and the like is meant those animals having impaired mental function, particularly memory impaired function, generally due to aging. Typically, the invention is of value to those mammals in the last 40%, preferably 30% of the expected life span of the mammal species.

The approximate dissociation constants for $Ca^{2+}$ of the above buffers are set out in following Table 1.

TABLE 1

| Chelator | Approximate $K_D$ |
|---|---|
| EGTA-AM | 100 nM |
| BAPTA-AM | 160 nM in 0 nM Mg |
|  | 440 nM in 1 nM Mg |
| 5,5'-$Br_2$BAPTA-AM | 3600 nM |
| 5,5'-$F_2$BAPTA-AM | 660 nM in 0 nM Mg |
|  | 706 nM in 1 nM Mg |
| 4,4'-$F_2$BAPTA-AM | 4600 nM in 0 nM Mg |

** Molecular Probes Inc. Eugene, Oregon.

The structures of BAPTA-AM and its derivatives are shown hereinbelow:
Wherein BAPTA: $R_1=R_2=H$
4,4'-$F_2$ BAPTA: $R_1=F_1$ $R_2=H$
5,5'-$F_2$ BAPTA: $R_1=H$ $R_2=F$
5,5'-$Br_2$ BAPTA: $R_1=H$ $R_2=Br$ The BAPTA-AM is de-esterified intracellulary to form the active chelating compound, by the process:

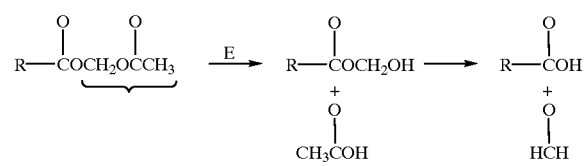

Thus, in one preferred method according to the invention, the results describe herein confirm that the cell-permeant calcium chelator, BAPTA-AM significantly improves spatial learning and memory in aged rats. Moreover, the results of the retention test revealed a long lasting positive effect of BAPTA on rats spatial memory. The analysis of rats' locomotor behaviour during the experiments did not reveal any apparent effects of BAPTA on swimming abilities, speed or rats searching paths.

The positive effect of BAPTA-AM on spatial learning was most pronounced in the first phase of the training period. The analysis of measures related to the acquisition of spatial information showed that BAPTA rats had not only shorter latencies of funding the escape platform, but they also showed better focal search in the correct part of the pool. The BAPTA rats spent consistently higher proportion of their search time in the target quadrant, and as a consequence had always shorter average distances to the platform position during the search. The concordance between various measures of spatial learning capabilities provides stronger support for the interpretation of obtained results. Although the escape latency, the proportion of time in target quadrant and the proximity measure are usually interrelated, interpreted together, they yield a more reliable picture of learning progression during training and reflect the systematic development of the spatial bias.

It is emphasized that the most significant effect of BAPTA-AM on spatial learning in aged rats was apparent in the first four–five days of the whole 8 day test. In the final phase of the training, both groups showed comparable performance. However, BAPTA rats persisted in having better scores in all measures of spatial learning. The control rats showed significant learning over time (significant day effect and lack of significant group by day interactions in all learning measures), but they were learning at a slower rate and their performance was never better than that of the BAPTA group. Although the aged rats are inferior in comparison to the young ones in acquiring spatial information in the water maze, given enough training time they eventually are able to perform at the comparable level. It is also possible that the "BAPTA effect" could rapidly reach a ceiling set either by physical capabilities of aged rats, or by other than increased level of intracellular calcium, changes in the CNS caused by aging, The method of the present invention is applicable for enhancing impaired mental function and to alleviate memory loss in mammals.

The membrane permeant calcium buffer may be administered, for example, by one of the following four routes, namely, intravenously, intra-arterially, intrathecally, i.e. within the membranes surrounding the nervous tissue, or intraventricularly, i.e. directly into the chambers inside the brain. The buffer is, typically, administered in a suitable vehicle, in which the active ingredient buffer is either dissolved or suspended in a liquid and which permits the buffer to be delivered from the bloodstream into the nerve cells, thereby crossing the blood brain barrier without undue toxicity or from the cerebrospinal fluid into nerve cells without undue toxicity. Solutions would be, typically, alcohol solutions, dimethyl sulfoxide solutions, or aqueous solutions containing, for example, polyethylene glycol containing, for example, polyethylene glycol 400, Cremophor-EL or Cyclodextrin. Such vehicles are well-known in the art, and useful for the purpose of delivering a membrane permeant calcium buffers to work, they must be administered in a solvent that would prevent them from precipitating in the otherwise aqueous environment of the bloodstream. The solvent dimethylsulfoxide, DMSO, is one such useful solvent. Thus, treatment of a patient with a membrane permeant calcium buffer is performed.

Preferably, the buffer is a chelating agent for the calcium ion, and more preferably, a buffer that is essentially calcium ion selective over other metal ions, such as for example, $Fe^{2+}$, $Mg^{2+}$, $K^+$ and $Na^+$. Calcium buffers having a $K_D$ selected from the range of $1 \times 10^{-4}$ to $1 \times 10^{-8}$ Molar are most preferred. Thus, specific BAPTA-like buffers of value in the present invention are BAPTA-AM; EGTA-AM; 5,5'-difluoro BAPTA-AM and 4,4'-difluoro BAPTA-AM, and 5,5'-dibromo BAPTA-AM, as hereinbefore defined.

In yet a further aspect, the invention provides pharmaceutical compositions comprising a cell membrane permeant calcium buffer as hereinbefore defined in admixture with a suitable pharmaceutically acceptable diluent, carrier or adjuvant when used for alleviating impaired mental function and to alleviate memory loss in aged mammals. It will be understood by the person skilled in the art that the pharmaceutically active cell membrane permeant calcium buffer should be present in pharmaceutically effective amounts.

In a still yet further aspect, the invention provides a process for the manufacture of a pharmaceutical composition when used for alleviating impaired mental function and to alleviate memory loss in mammals, preferably aged mammals, said process comprising admixing a cell membrane permeant calcium buffer with a pharmaceutically acceptable carrier therefor.

In yet a further aspect, the invention provides pharmaceutical compositions comprising a cell membrane permeant calcium buffer as hereinbefore defined in admixture with a suitable pharmaceutically acceptable diluent, carrier or adjuvant when used for reducing the recovery time from anaesthesia in mammals.

Thus, in one preferred method according to the invention, the results described herein confirm that the cell-permeant calcium chelator, BAPTA-AM, significantly reduces the recovery time from anaesthesia for an aged mammal under anaesthesia.

In a still yet further aspect, the invention provides a process for the manufacture of a pharmaceutical composition when used for reducing the recovery time from anaesthesia in mammals, preferably aged mammals, said process comprising admixing a cell membrane permeant calcium buffer with a pharmaceutically acceptable carrier therefor.

In a preferred aspect, the invention further provides a method as hereinabove defined wherein said buffer is administered in the presence of a pharmaceutically acceptable anion transport inhibitor. The preferred anion transport inhibitor is probenecid, which is preferably administered through intraperitoneal injection prior to administration of the calcium buffer.

BRIEF DESCRIPTION OF THE DRAWINGS

In order that the invention may be better understood, preferred embodiments will now be described, by way of example only, with reference to the accompanying drawings, wherein.

DETAILED DESCRIPTION OF PREFERRED EMBODIMENTS ACCORDING TO THE INVENTION

EXPERIMENTAL METHODS

Experimental Methods Relating to Spatial Learning

Figure 1A:
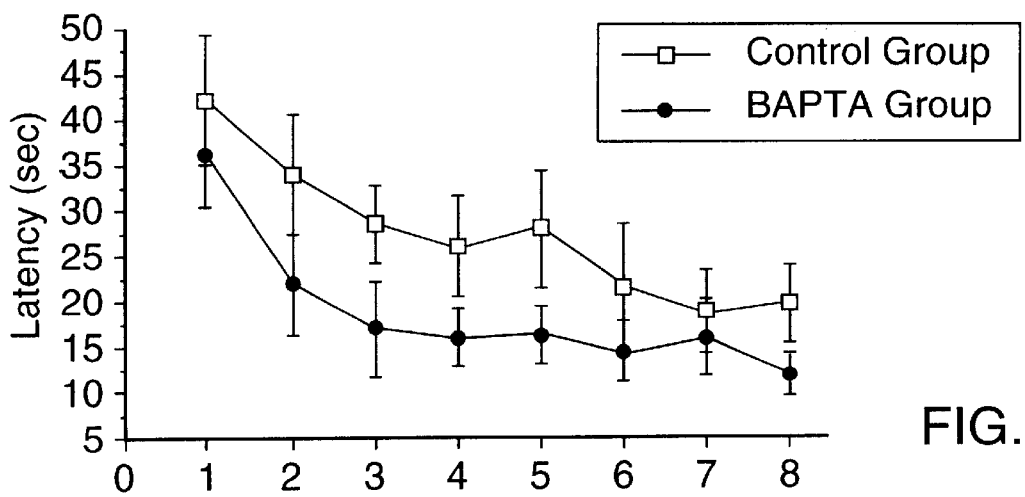
FIGS. 1A–1C represent graphs of the performance of aged BAPTA-AM treated and control rats during training sessions.

Two pilot experiments preceded the main experiment of the study. The core of the methodology was common to all experiments and is described in detail in this section referring to the main experiment. Any procedural differences and/or additional details are given in the description of each pilot experiment. Subjects.

Fisher 344 male rats, 22 months old at the beginning of behavioural testing were used in the study. Seventeen animals were purchased from the National Institute of Aging, Maryland, U.S.A. They were pathogen-free at the arrival, and were kept individually in standard plastic rat cages with water and food ad libitum. The colony room was maintained on 12:12 LD photoperiod (7:00 AM, lights on), with the ambient temperature at $21\pm1°$ C. and relative humidity at 55%. All animals were kept for two weeks to acclimatize to the new conditions before the experiment commenced. One week before the experiment, all animals were handled twice per day, and their general health and body weight were monitored. While handling, each rat was gently taken by its shoulders, lifted from the home cage and placed in a new cage. After 10–15 seconds it was carried back to its home cage. All behavioural tests were carried out in the light phase of the LD cycle, and all rats were experimentally naive at the beginning of the experiment.

Drugs Dosages and Administration

BAPTA-AM, dissolved in dimethyl sulfoxide (DMSO), was used in a dose of 5 mg/Kg. To increase longer retention of BAPTA-AM in the brain, the drug was administered in the presence of probenecid (25 mg/kg), an anion transport inhibitor used clinically(31). All drugs were administered through intraperitoneal (ip) injection each day before testing. Probenecid was administered to all rats 1.5 hours before the test, followed by the injection of BAPTA-AM to experimental and DMSO to control groups half an hour later. The test commenced one hour after the last injection and lasted usually for 1.5 to 2 hours.

Experimental Procedure

A procedure to assess spatial memory in the water maze involves the demonstration of spatial discrimination by the tested subjects. A submerged escape platform was placed in the water tank and a rat had to locate and escape onto this platform by using available extra maze spatial cues. The successful solution of this test, however, depends not only on intact spatial memory, but also on intact locomotor and exploratory abilities, and the development of appropriate search strategies (32,33). Aged rats show considerable variability of learning impairment within an age cohort (34). In order to identify the characteristics of performance of each individual in the water maze, the spatial training was preceded by a non-spatial training (32,35).

Water Maze Apparatus.

The water maze apparatus was a round, black pool 1.65 m in diameter located in one half of a large room (8×4.5 m) with various distant spatial cues. The minimum distance of the pool to the nearest visible cue was 2 m. Additional black posters (one per wall) were placed on the three walls closest to the pool.

The hidden platform, made of clear plastic with a serrated surface, was submerged 1.5 cm under the water level which was 30 cm below the rim of the pool. The temperature of water was at $26\pm1°$ C. at the beginning of the test. By the end of testing the water temperature never dropped below $25\pm1°$ C. The water in the pool was kept clear and the light in the room was provided by two 150 W halogen lamps placed on the floor with beams directed towards white painted walls. This arrangement provided diffused light which did not interfere with the tracking system used for data recording. Each rat was gently lowered into water, facing the wall of the pool, and allowed to swim for 60 sec. After funding and climbing the platform, it was allowed 10 seconds on the platform, after which it was placed back in his home cage beneath a heat lamp. If a subject did not fund a platform within 60 second period, it was gently guided by an experimenter towards it where it remained for 10 seconds. Each day of testing consisted of 3 trials separated by 30–40 minutes from each other. During all tests the rack with rats' cages was in the second half of the experimental room, while the experimenter withdrew to the adjacent room to monitor the progress of the test on the tracking system.

Non-spatial Training and Experimental Groups Formation

Non-spatial training was conducted on undrugged animals for 4 days, 3 trials per day. During each trial the hidden platform was moved randomly between 5 different positions (four centers of pool quadrants and the middle of the pool), and subjects were released from randomly chosen cardinal points (N, E, S, W) along the wall of the pool. At this stage white curtains surrounded the pool eliminating most extra-maze spatial cues. It was impossible to eliminate all visual extra maze cues completely (the halogen lights were always in the same place and the glow was visible through the curtain), as well as there was no control regarding auditory cues, the presence of the curtain together with random release points and changing platform positions made any cue unreliable, forcing subjects to search randomly for the platform. To increase the likelihood of funding the platform through a random search, each subject was given 90 seconds of swim in all trials of non-spatial phase. The non-spatial training was used first, to familiarize the animals with non-spatial components of the task, like the fact that the platform provided an escape from water, and that it was positioned away from the wall of the pool. During this stage, rats, decreased, initially, observed wall-hugging behaviour (30) and learned more efficient search strategy. Second, using rats performance during non-spatial training, and checking their weight, individuals with locomotor impairments and/or sudden deterioration of their physical conditions due to swimming were excluded from further studies.

The weight of two rats dropped after the first day of the non-spatial training and they showed obvious signs of exhaustion when swimming. These rats were excluded from the experiment leaving 15 subjects. At the end of the non-spatial phase, another rat was excluded due to sudden decrease of weight from 425 to 396 g (average for the whole group was 435 g), leaving 14 rats with no obvious swimming deficits and stable weight. The rats were then ranked from the most efficient to the least efficient swimmers on the basis of their search time in the last two sessions of non-spatial training. Using these ranks, subjects were allocated to two groups (N=7 per group) with an equal proportion of good and bad performers. One of the two groups was then randomly allocated to experimental (BAPTA-AM), while the other served as a control group.

Spatial Training.

The spatial training started 3 days after the end of non-spatial training, and lasted for 8 days with 3 trails per day. During this phase the curtain surrounding the pool was removed and the platform was always placed in the same spatial position of the pool (center of NW quadrant). Subjects were released from points along the wall in the middle of quadrants NE, SE, and SW. Placing the points of release further away from the quadrant (NW) containing the platform prevented subjects funding it by chance just after their release. The points of release were chosen randomly and the rats were allowed 60 seconds of swimming, with 10 seconds on the platform after climbing onto it The day after the end of spatial training, all rats were given a probe trial to assess their development of spatial bias. During the probe trial, the platform was removed from the pool and each rat was given 60 seconds of swimming.

Retention Test

After the completion of the learning acquisition phase, all animals were kept for 35 days in their home cages with food and water ad libitum. Apart from weekly cage cleaning and routine health checks twice per week, the animals were not disturbed. No drugs were administered in that time. After that period, all animals were given a retention test. The test was given in the same experimental room, with all spatial cues and platform position in exactly the same place as they were during the learning acquisition training. The handling procedure before and during the retention test was similar to the training procedures, but no drugs were given to the rats.

The test lasted for 4 days with 3 trials per day. All other procedural details were kept the same as during spatial training.

Data Recording and Behavioural Analysis

The behaviour of rat in the pool was recorded by a camera suspended 2.5 m above the center of the pool, connected to a video tracking system (HVS Image Advanced Tracker VP200) and a PC computer running HVS software developed by Richard Baker of HVS Image, Hampton, UK. All recording equipment was placed in the room adjacent to the experimental one. In addition to standard measures of platform search time (latency) and the percent of time spent in each quadrant of the pool, the length of swim path, swim speed, percent of time spent floating (defined as swim movements with speed below 5 cm/s), and proximity of the rat's search to the goal (7) were also analyzed. The proximity provides a measure of the rat's development of a spatial bias during training This measure was derived by sampling the position of a rat in the pool 10 times per second to provide a record of its distance from the platform in 1 second averages. Therefore when a rat searches for the platform close to its position, it's average proximity measure is low. The swim speed was adjusted for occasional floating bouts and presented as active swim speed.

Two scores were calculated to assess the accuracy of search for the platform during the probe trial. A site-preference score, calculated as the number of crosses over the target site, minus the mean of crosses over alternative sites in other quadrants, and a search-time preference score, i.e., the amount of time spent in the trained quadrant of the pool minus mean time in the alternative quadrants (36).

The data were analyzed with analysis of variance ANOVA. Whenever data showed significant departure from homogenity of variance, the degrees of freedom were reduced by Greenhouse-Geissser epsilon correction for heterogenity of variance (37). Comparisons between two independent groups were carried out using the two-tailed Student t-test. The critical $\alpha$ level was set to 0.05 for all statistical analyses.

Pilot Experiments

The effects of BAPTA on the behaviour of aged Fisher 344 rats were addressed in two pilot experiments. Detailed analysis of rats behaviour and their swimming abilities after injection of probenecid followed by DMSO, and of probenecid followed by BAPTA helped refinement of the experimental procedures and dosages of the drugs.

In the first pilot experiments, four 24 months old Fisher 344 rats were used. The animals were handled before the experiment, and underwent non-spatial training for 4 days with 3 trials per day. The drugs, at dosages: probenecid—35 mg/kg, BAPTA—10 mg/kg, were injected following the schedule described in the general methods. Since adult rats are capable of rapid learning of spatial information within 1 day, with 10 acquisition trials (33), the rats were trained for 2 days with 8 trials per day (two blocks of 4 trails separated by 2 hour period).

The small sample size of 2 rats per group excluded any meaningful statistical comparisons. However, the eyeball examination of data obtained in the first day did not reveal any disproportionate differences of magnitude larger then two SEMs during training and the probe trial between rats injected with probenecid plus BAPTA, and probenecid only. It was observed, however, that all rats showed signs of exhaustion after the $8^{th}$ trial in the first day. In the second day, the number of trial was reduced to 6. The mean escape latencies averaged across all 6 trials of day 2 of training were similar for control and BAPTA rats (48.7 seconds, and 49.7 seconds, respectively). The swim speed for both groups was 20.76 and 19.39 cm/second, respectively. However, the BAPTA rats showed, on average, a more focused search for the platform, in spending 36.6% of their search time in the target quadrant, which contained the hidden platform, and in contrast to the controls which dwelled in that quadrant for 26% of their time, which is a score very close to a random search (25%). Closer examination of the rats' performance in the last trials of the second day (trials 5 and 6 combined) also pointed at better performance of the BAPTA rats. They reached the platform within 40.65 seconds in contrast to 60.0 seconds of the control rats, and spent 41.68% of their time in the target quadrant as compared to 28.0% of the controls.

The small sample size and large variability of the scores made it difficult to draw any firm conclusion in regard to the effects of BAPTA on learning. Although no profound differences were noticed in any measures between BAPTA and control rats during swimming, observation of BAPTA rats behaviour after swimming revealed that they were less active in grooming and other drying activities, such as for example moving towards a heat lamp or shaking of the body.

In the second pilot experiment, the dose of BAPTA was lowered to 5 mg/kg in order to eliminate rats inactivity during inter-trial periods. The sample size was increased to 6 rats per group and the training procedure was modified. Since the results of the first pilot experiment indicated that 8 trials per day were too demanding, the rats were trained for four days with 3 trials per day. After the last trial of day 4, all rats were given the probe trial.

One month after the last day of spatial training and drug injection, the rats were given a retention test. The test was given in the same room with all spatial cues and the platform position unchanged. The retention test was carried out during two consecutive days. In the first day, no drugs were given, while during the second day the groups were injected with appropriate drugs before the test. The analysis was performed on pooled data across all trials for each day of training and did not reveal any significant group differences in latency, path length, swim speed, and percent of time spent by the groups in the target quadrant. Inspection of the latencies for each day of training revealed that the groups showed similar performance during the first 3 days of training, while on day 4, the BAPTA group showed a clear tendency to a shorter latency for reaching the platform (BAPTA—24.1 seconds, Controls—37.3 seconds; t(10)= 1.65, p=0.1). During the probe trial, although both groups spent the same percent of time in the target quadrant, the BAPTA rats were significantly better in their accuracy of swimming over the platform position (x=1.8—BAPTA, x=0.5—Controls, t(10)=−2.27, p<0.05). The retention test did not reveal significant differences in the escape latency or in other measures between the groups. However, while group latencies during the first day of the retention test were similar (29.8 and 26.0 seconds for control and BAPTA rats, respectively), on the second day, the BAPTA groups showed shorter (14.6 versus 24.0 seconds for controls), although not significant escape latency (t(10)=1.41, p=0.2). Also, all rats were equally active in their drying behaviours during inter-trial periods.

The results of the second pilot experiment indicated that BAPTA at the dose of 5 mg/kg showed beneficial effect on spatial learning on the $4^{th}$ day of training. This was confirmed by the probe trial in which BAPTA rats showed better search strategy. A retention test administered one month after the last injection of the drug revealed that the BAPTA rats maintained the tendency to perform better in the learned spatial task. The design of the experiment did not allow elucidations of whether the effect was due to a cumulative effect of BAPTA administered during training, or due to the one injection of the drug at the beginning of the second day of the retention test. The above question was addressed in the main experiment of the study.

EXPERIMENTAL METHODS RELATING TO REDUCED RECOVERY TIME

Phase I: Effects of BAPTA-AM on Anaesthetic Actions in Aged Hippocampal Neurons

Slice Preparation.

Old (24–27 months) Fisher 344 rats were decapitated under halothane anaesthesia. The brain was quickly removed and submerged for two minutes in oxygenated (95% $O_2$–5% $CO_2$) iced artificial cerebrospinal fluid (ACSF) containing (in mM): NaCl 125, KCl 2.5, $NaHCO_3$ 26, $NaH_2PO_4$ 1.25, $CaCl_2$ 2, $MgCl_2$ 2 and glucose 10. Whole brain slices (400–500 $\mu$m thick) were obtained using a Vibroslicer. Slices were then incubated at 30–31° C. into a humidified holding chamber and allowed to recover for at least 1–2 hours before recording.

Drug Preparation and Application.

The volatile anaesthetic, isoflurane (Anaquest, Pointe Claire, Quebec), was vaporised at 1.5 l.min$^{-1}$ flow rate with 95% $O_2$–5% $CO_2$ mixture at 23° C. ambient temperature using an Ohmeda vaporiser (Ohio Medical Products, Madison, Wis.). Isoflurane vapour was then bubbled in ACSF reservoirs (inverted 60 ml syringes) for a minimum of 20 min. before bath application at designated volume/volume concentration values. Isoflurane vapour also was introduced into the chamber atmosphere immediately above the submerged slice. The volume/volume concentration values (vol. %) are the concentrations of isoflurane bubbled into the superfusate which are produced by the vaporiser. Previous studies have shown that there is a linear relationship between the anaesthetic concentrations in the bubbled superfusate and the concentrations in the superfusate reaching the slice (49,50). In the latter investigations isoflurane was measured in the perfusing medium by 19-Fluorine nuclear magnetic resonance spectroscopy.

BAPTA-AM (25 mg) was initially dissolved in a vehicle, dimethyl sulfoxide (DMSO; 1.25 ml) to obtain a stock solution. Before BAPTA-AM was diluted in ACSF to the desired concentration(25 $\mu$M), all phosphate buffers were substituted by HEPPES buffer to prevent any possible precipitation of BAPTA-AM molecules. The final concentration of DMSO in ACSF containing BAPTA-AM was 0.06%.

Experimental Design

Slices prepared from every animal studied were randomly incubated and perfused with one of two perfusates: (1) ACSF containing the vehicle (0.06% DMSO) or (2) ACSF containing BAPTA 25 $\mu$M with the vehicle 0.06% DMSO. Therefore, for every animal, recordings were obtained from slices incubated with the control and the treatment solution.

Electrophysiological Recording

Slices were transferred to a submerged recording chamber and continuously perfused with oxygenated ACSF. The flow rate of the perfusate was set at ~2 ml/min. All experiments were performed at 35.5±0.5° C.

Extracellular recording micropipettes (2–5 MΩ tip resistance) pulled from this walled-borosilicate capillary tubing, were filled with 150 mM NaCl. Dendritic fEPSPs were recorded from the stratum radiatum. A bioplar concentric stimulating electrode was placed either along the Schaffer collateral for orthodromic stimulation. Field potentials were evoked at 0.05 Hz. Stimulating intensities were adjusted to evoke ~75% of the maximal field potentials obtained with supramaximal currents. Extracellular signals were processed by an Axoclamp 2A amplifier (Axon Instruments, Foster City, Calif.). Data were acquired, stored and analysed using an IBM clone computer and P-Clamp software, version 5.1 and 6.0 (Azon Instruments, Foster City, Calif.). A slice was considered stable when the orthodromic response varied less than 5% over a fifteen minute intervals. Additionally, a slice was included in the study if the amplitude of the dendritic field and the population spike were greater than 1.5 and 2 mV in amplitude, respectively. Input/output (I/O) curves were determined by signal averaging of 3–4 consecutive runs of 5 stimulation intensities ranging from those evoking minimal to maximal response.
Data Analysis.

FEPSP peak amplitude was considered to be the distance between the isoelectric line and the peak downward deflection. The duration of the fPSP was measured from the onset to the offset of the synaptic transient, respectively. The rate of rise of fEPSPs was considered the first derivative of the interval of the rising phase included between 10% and 90% of the change. Percentage of isoflurane-induced depression of peak amplitudes was calculated as follows: (control response-isoflurane response/control response)×100. Percentage of recovery from isoflurane actions normalised to control measurements was determined using the following expression: (recovery response—control response/control response)×100. Raw data as well as percentages of isoflurane-depression and recovery obtained from aged slices incubated in BAPTA were compared to similar measurements taken from aged slices incubated in control solutions containing only the vehicle (0.06% DMSO) using one-tailed student t-test for independent samples. The software SPSS version 6.1.2 (SPSS Inc., Chicago-Ill.) was used for the calculations. Statistical significance was always assumed to be accepted at p<0.05.

Phase II: Effects of BAPTA-AM Injection on Anaesthetic Requirements and Post-anaesthesia Recovery Time in Old Fisher 344 rats The anaesthetic requirements of isoflurane is the minimum alveolar concentration (MAC) value. MAC is defined as the anaesthetic concentration that produces somatic movement in 50% of animals subjected to a standardized painful stimulus. The recovery time in these investigations was the time taken just after the inspired isoflurane concentration drops to zero, i.e. termination of anaesthesia to the time when the animal spontaneously resume the righting reflex (normal posture). All animals were in the supine position during anaesthesia.
Experimental Design.

Five old Fisher 344 rats (males: 24–26 months old) were included in this phase of the study. Control measurements of MAC and recovery time were determined for every animal before BAPTA-AM injection. MAC and recovery time were determined the following day after BAPTA-AM administration by one hour and thirty minutes. The animal was then kept at the animal care facility and studied after 72 hours of treatment to test long term effects of BAPTA-AM.
Drug Administration.

Before BAPTA-AM injection, probenecid 2.5 mg.kg$^{-1}$ was injected intraperitoneally (I.P.) using a 25 G needle. Probenecid was dissolved in saline alkalinised with NaOH to pH=8.0. The final concentration of probenecid was 12 mg.ml$^{-1}$. Probenecid was expected to increase the accumulation of BAPTA in the neurons because it blocks BAPTA-AM extrusion from cells. BAPTA-AM was dissolved in DMSO to a final concentration of 20 mg.ml$^{-1}$. BAPTA-AM 10 mg.kg$^{-1}$ was injected I.P. after 30 min of probenecid administration. MAC and recovery time determination was always done 90 min after BAPTA-AM injection.
MAC Determination.

All experiments were performed in mid morning to midafternoon to minimize the possibility of circadian variation. The rectal temperatures of the rats were maintained at 34.5–35° C. by using radiant heat from a headlight lamp. The inspired concentration of isoflurane was continuously measured by an infrared gas analyser (Datex Capnomac II, Puritan Bennett, Pickering, Ontario, Canada). The heart rate was monitored by an electrocardiogram monitor and the respiratory rate was measured visually. The anaesthetic circuit used was a modified Mapleson D circuit with a tightly fitting mask at the animal end. High oxygen flow rates (3 l.min$^{-1}$) were used to ensure that the circuit function as a non-rebreathing circuit. The inspired isoflurane concentration was measured by inserting the tip of a 1.5 inch 16G angiocatheter in close proximity of the animals nostrils during the application of the tight fitting mask. The angiocatheter was attached to the gas analyser by standard tubing. The volatile anaesthetic, isoflurane (Anaquest, Pointe Clare, Quebec, Canada), was vaporised at 3 l.min$^{-1}$ oxygen flow rate at 23° C. ambient temperature using a recently calibrated Ohlmeda vaporiser (Ohio Medical Products, Madison, Wis., USA). Animals were initially anaesthetised with isoflurane in a closed chamber. Then, they were placed on synthetic heat insulting pad and the anaesthetic circuit was tightly applied to their face. Anaesthesia was tested for in 0.125% increments in the inspired concentration of isoflurane starting with 0.5%. At each increment, the flick-tail response was tested by applying a 40 watt lamp to the junction of the middle and distal third of the tail for 15 s. Any somatic movement of the head, limbs or torso of the animal was considered a positive response. When no response was obtained; the inspired concentration was then decreased until movement following tail clamping. In all cases, the total duration of the study was 1–1.5 hours and in all cases 15 minutes were allowed between testing to allow for stabilization of the alveolar gas concentrations. MAC was calculated by the method described previously, MAC= (least concentration with positive tail-flick test+maximal concentration with negative tail-flick)/2 (51,52).
Recovery Time Determination.

At the end of the study, every animal was anaesthetised with 1× & 2× MAC determined using the above method. After 20 minutes of anaesthesia, isoflurane vapour was turned "off" and once the inspired isoflurane concentration dropped to "zero", the animal was kept on his back and the time for resuming normal posturing, i.e. resumption of the righting reflex was recorded.
Data Analysis.

MAC and recovery times before and after treatment were compared using non-parametric two-way ANOVA. Multiple comparisons were done using Mann-Whitney U-test.

RESULTS

Figure 1B:
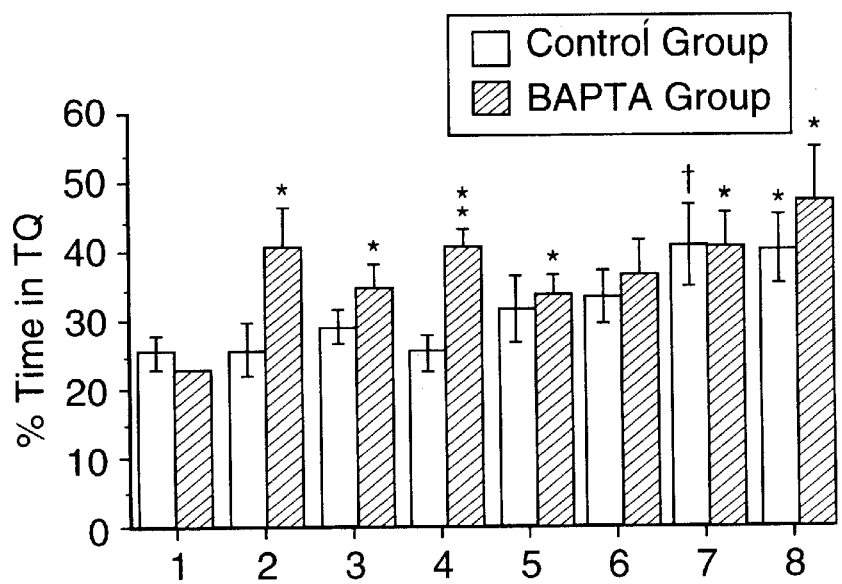
Figure 1C:
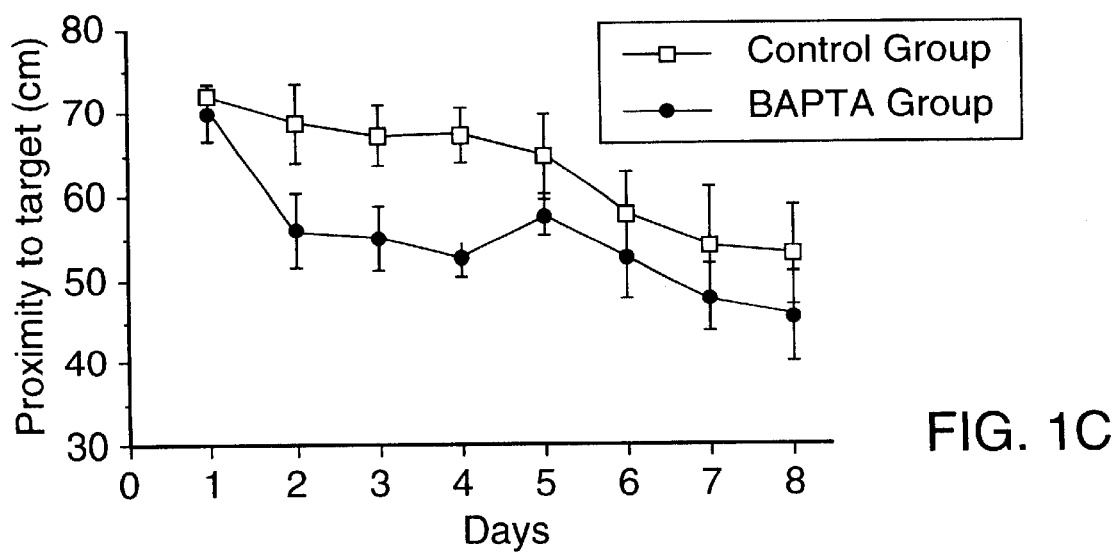

With reference to the drawings, FIGS. 1A–1C are the mean of three trials wherein FIG. 1A represents the average escape latencies to reach an escape platform; FIG. 1B the percent of time spent by rats in the target quadrant containing the platform wherein the average performance of groups in each day was compared against chance level (25%); and FIG. 1C the average proximity to the platform location for the groups (see Data Recording and Behavioural Analysis for details). Vertical lines represent SEM, panels A and C, see text for results of statistical analysis. Panel C, * p<0.05, ** p<0.001, p=0.06, comparison against the chance level of 25%.

Figure 2A:
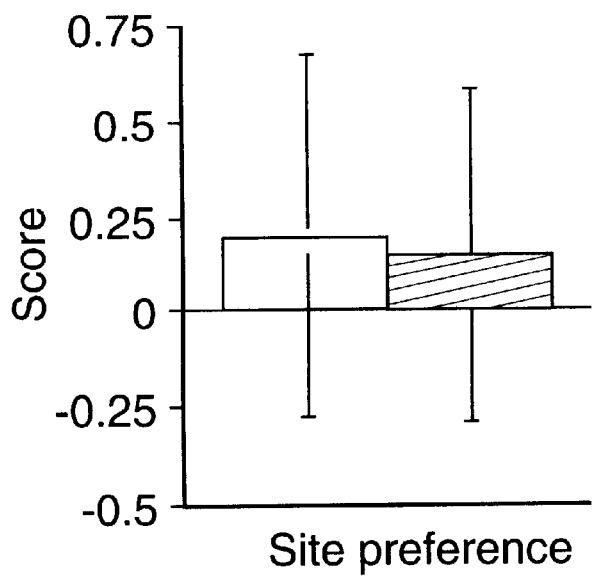
FIGS. 2A and 2B represent water maze preference scores for BAPTA-AM and control rats during the probe trail.
Figure 2B:
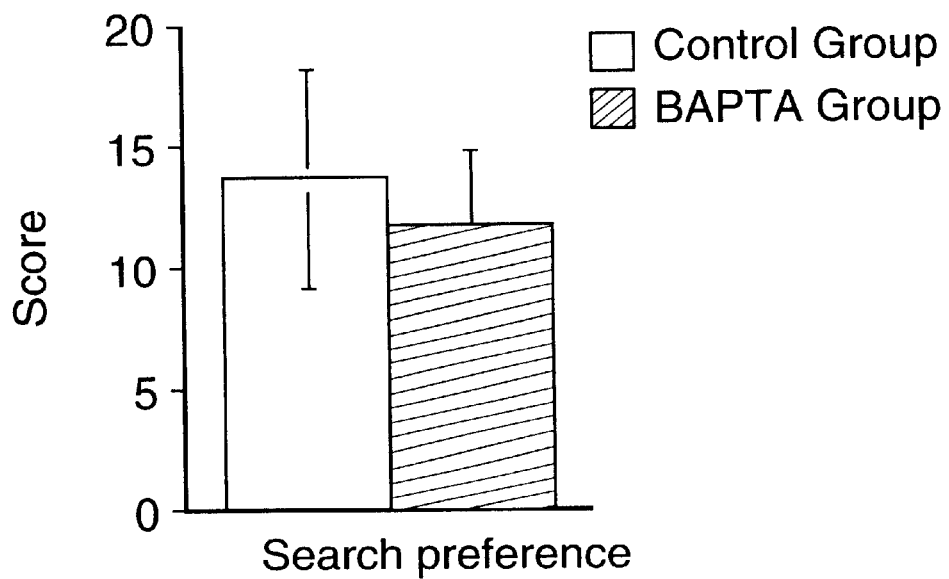

FIG. 2A provides the site preference score and represents the number of crosses over the platform position minus the average of crosses over the alternative sites in the other 3 quadrants; and FIG. 2B the search-time score represents the amount of time spent in the target quadrant of the pool minus average time spent in alternative quadrants. Bars represent means±SEM.

Figure 3A:
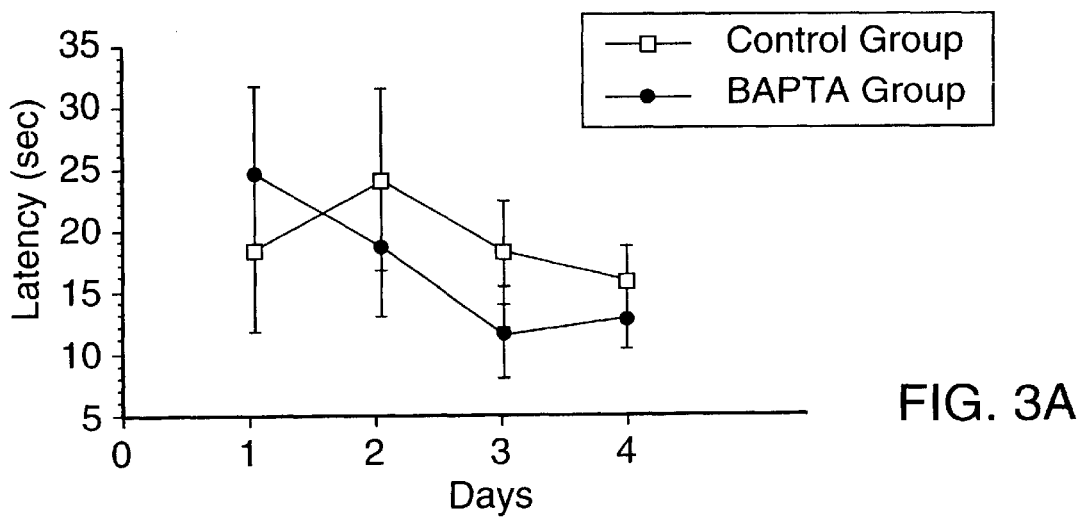
FIGS. 3A–3C represent graphs of the performance of groups in a retention test.
Figure 3B:
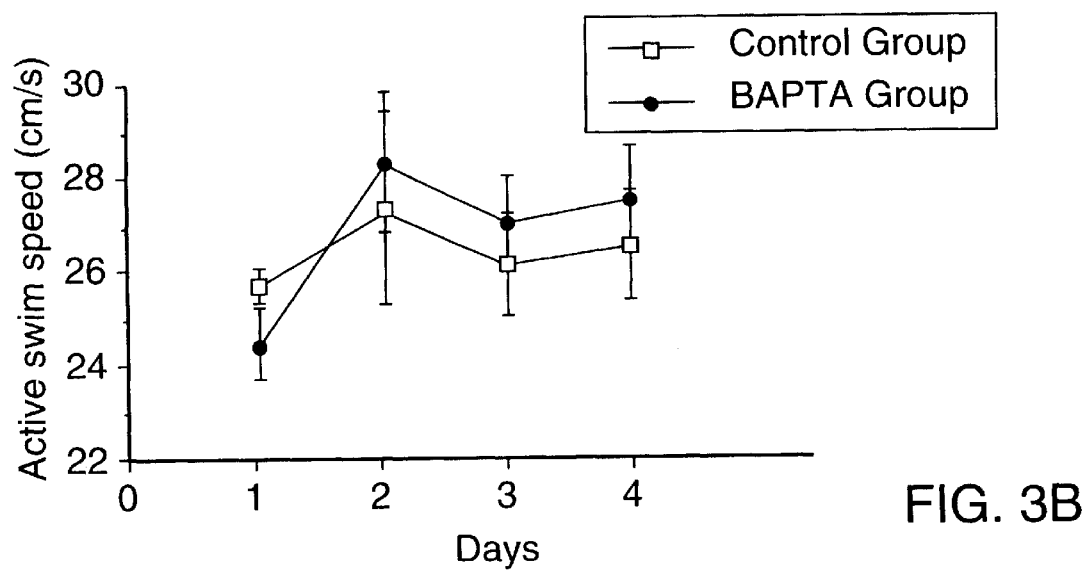

FIGS. 3A–3B represent performance carried out 35 days after the last day of training and wherein no drugs were administered to the rats at that stage of the experiment. FIG. 3A provides the average escape latencies to reach the platform; FIG. 3B the average active swim speed; and FIG. 3C the average proximity distance to the platform. Vertical lines represent SEM.

Non-spatial Training

Naïve to-the-water maze rats significantly improved their search for the platform when all extra-maze cues were obscured. Their average latency to fund the submerged platform significantly decreased from 66 seconds in the first day to about 39 seconds on the last day (F(3,39)=6.23, p<0.001). During the first two days, the rats showed a considerable amount of wall-hugging behaviour (78% and 72% respectively) and floating along the walls. These behaviours caused an initial decrease in swim speed (17.4–21.4 cm/second) which increased significantly after the rats learned to search actively throughout the whole pool (F(3, 39)=21.04 p<0.001). The swim speed within the last two days of non-spatial training stabilized at about 24 cm/second.

The result of non-spatial training demonstrated that the rats were capable of significantly reducing their search for a hidden platform when the extra-maze spatial cues were obscured and the position of the platform changed from trial to trial. At the end of the non-spatial training, all rats searched the whole pool in a systematic way, spending equal amounts of time in each quadrant of the pool.

Spatial Learning

All rats were actively swimming during the whole duration of the learning acquisition test. However, one rate from the control group developed persistent wall hugging swimming from the third day of testing and its scores were excluded from the analysis.

The analysis revealed that the BAPTA rats had significantly shorter escape latencies than control rats (F(1,11)= 5.48, p<0.05, FIG. 1A). With the exception of swim path, none of the other measures significantly differentiated the groups during the test. BAPTA rats showed a tendency to have shorter swim paths (F(1,11)=4.52, p=0.06). This result was expected since the escape latency and path length were positively correlated measures because the rats in both groups had similar swim speeds. More rapid acquisition of spatial information by BAPTA rats was substantiated by the analysis of the proportion of time spent in the quadrant of the pool containing the escape platform (FIG. 1B). The BAPTA rats developed significantly higher than random spatial bias as early as the second day of training, while the control rats showed significant above chance search only during the last two days of the test. A purely random search for the platform usually resulted in an equal proportion of time (25%) spent in each quadrant. The animal demonstrated a positive bias for a given spatial location when it spent an increased proportion of time searching in the close proximity of the target place. The stronger spatial bias for the escape platform position of BAPTA rats was also reflected by their shorter, although, not significant, average proximity to the platform (FIG. 1C). This measure takes into account the subject's total swim path with reference to the platform position and not only the time spent in the target quadrant.

It was noticed that both BAPTA and control rats showed a significant improvement in funding the escape platform as a result of training. The effects of training days for the latency, percent of time in the target quadrant and the proximity measure were statistically significant (all ps<0.01). In none of the above measures was significant interactions between group and days found. The above results demonstrate that although all rats learned the position of the platform, the BAPTA rats were substantially better.

The analysis of rats' locomotor behaviour during the test did not differentiate the BAPTA rats from controls. The observed floating level was between 2 and 5%, (not significant for group, days, and group by days interaction) and was very similar to the amount of floating shown in the last two days of the non-spatial training (3.3–5%). The swim speeds during the acquisition phase (23–26 cm/second) and the probe trial (24 cm/second) were also similar to the swim speed during the last two days of the non-spatial training (24 cm/second).

Accordingly, the examination of the results related to rats' swimming abilities and active search excluded the notion that BAPTA could significantly affect other behavioural systems, such as motivation to swim or search, or cause significant changes in the peripheral nervous system. The results strongly indicated that BAPTA significantly enhanced the spatial learning capabilities of aged rats. The examination of groups scores revealed that the most profound effect of BAPTA was seen during the first half of spatial training (FIG. 1). To substantiate this observation, the groups' performance in the latency, percent of time in the target quadrant, and proximity was compared within the first 5 and the last 3 days of training. This comparison revealed that during the first 5 days of training the BAPTA rats had significantly faster escape latencies (F(1,11)=6.47, p<0.05), spent more time in the target quadrant (F(1,11)=4.42, p<0.05), and had shorter proximity measure (F(1,11)=6.5, p<0.05). Both groups showed a significant learning effect across days within that period (0.05 <ps<0.01), and in the case of the percent of time in the target quadrant, a significant interaction between the group and days was found (F(4,44)=2.64, p<0.05). This interaction was caused by much faster development of spatial bias which was visible already on day 2 of training, (FIG. 1B) by BAPTA rats.

In contrast, none of the three measures of spatial bias was significantly different between the groups in the last three days of the test, although the BAPTA rats continued to have better scores in all learning measures (FIG. 1).

The rats of both groups showed similar performance in the probe trial. Groups' preference and search scores during the probe trial are shown in FIG. 2.

In conclusion, the results showed the positive effect of BAPTA on spatial learning in the aged Fisher 344 rats. This effect was particularly pronounced in the initial stages of learning and facilitated the acquisition of spatial information. The analysis of rats' locomotor behaviour in the test did not reveal any non-specific effects of BAPTA on behaviour which could bias the main results. The control rats showed comparable performance at the end of training period, but they never got better than the BAPTA rats.

Retention Test

Two control rats and one BAPTA rate died during the period preceding the retention test, which reduced the sample size to 6 BAPTA and 5 control rats. Furthermore, the control rat showing persistent wall-hugging swimming during training, continued performing this behaviour during the retention test. Its' scores, therefore, were removed form the analysis and reduced the sample size of the control group to 4 animals.

Figure 3C:
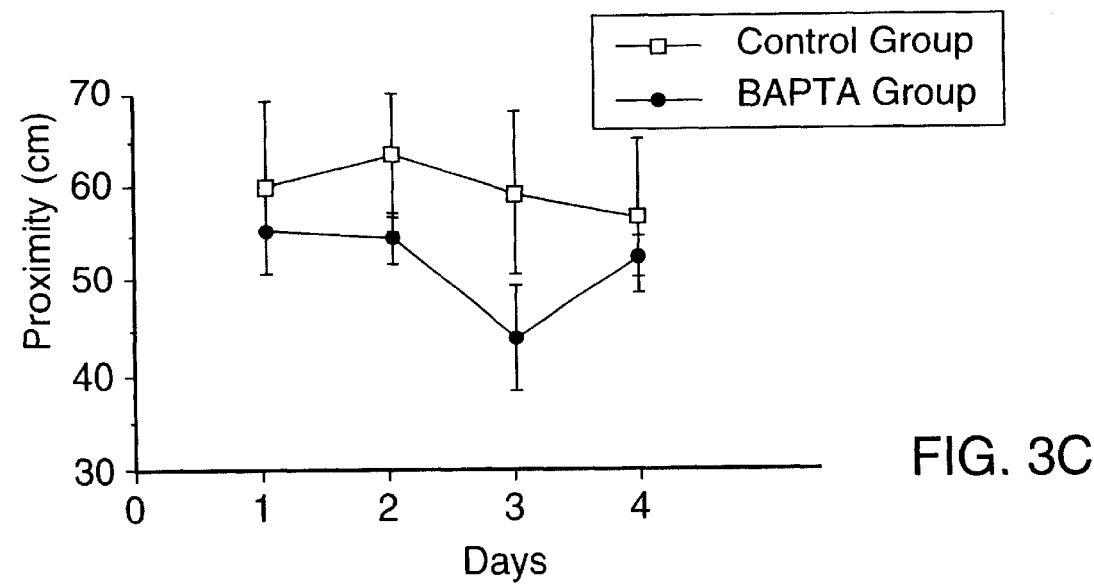

The analysis of the rats' behaviour during the retention test did not reveal any significant differences between groups or group-by-days interaction in any measured variable. The results of escape latency, average proximity to the platform during search and swim speed are presented in FIG. 3. It is important to notice that the BAPTA rats continued to show a tendency of better performance in the test. Their escape latencies were shorter than the latencies of the control rats apart from the exception of the first day of the test, (FIG. 3A) and the proximity measure was always smaller than the score of control rats in each day of the test (FIG. 3C). Since the swim speed of both groups was similar (FIG. 3B), this result indicates that after a period of 35 days, the BAPTA rats continued to show signs of improved spatial behaviour.

Phase I: Effects of BAPTA-AM on Anaesthetic Actions in Aged Hippocampal Neurons In a control study to determine the effects of DMSO on fEPSPs in aged slices ACSF containing DMSO 0.06% & 0.12% was applied continuously for about 18 min to 7 & 8 aged slices, respectively. Over the 18 minute application period, no effect on the fEPSPs' amplitude, rate of rise or area was ever observed.

The effects of isoflurane (2%) applications were observed on 22 old slices. Ten slices were incubated in control ACSF containing 0.06% DMSO and 12 slices were incubated in ACSF containing BAPTA-AM 25 $\mu$M dissolved in the vehicle 0.06% DMSO. The maximal effects were evident at 6–8 minutes with a perfusion rate of ~2 ml/min. To ensure reproducibility of isoflurane effects, the same vapour concentration was applied 2–3 times to the same slice in about 40% of experiments. The consistent reproducibility of isoflurane effects indicates that the anaesthetic concentrations did not fluctuate at the site of action within the hippocampal slice. Steady-state isoflurane concentrations in the slice were ensured by using relatively fast perfusion rates (~2 ml/min), bubbling the perfusate with isoflurane for at least 20 minutes before application and introducing the anaesthetic vapour into the chamber atmosphere immediately above the slice.

Isoflurane application depressed the orthodromically evoked fEPSPs produced by using submaximal stimulation (~75%) in all the slices taken from old animals. In order to eliminate the possibility that a particular subset of excitatory synapses were sensitive to the anaesthetic at submaximal stimulation, the effect of isoflurane 2% on different stimulation intensities was examined by generating an input/output (I/O) relationship. The effect, i.e. reduction of the field amplitude, was observed at all stimulation intensities suggesting that this phenomenon is not peculiar to a small number of synapses.

Isoflurane 2% consistently depressed fEPSPs amplitude, area and rate of rise. However, aged slices incubated and perfused with BAPTA-AM showed resistance to isoflurane actions. Table 1 shows the effect of BAPTA-AM application on isoflurane actions in aged hippocampal slices.

TABLE I

|  | Vehicle (n = 10) | BAPTA-AM (n = 12) |
| --- | --- | --- |
| fEPSP Amplitude (mv) | | |
| Control | 5.49 ± 1.74 | 6.97 ± 2.20 |
| Isoflurane | 3.35 ± 1.23*# | 4.58 ± 1.36*# |
| Recovery | 5.60 ± 2.01 | 7.64 ± 2.38*# |
| EPSP Area (mv.ms) | | |
| Control | 60.88 ± 15.36 | 70.76 ± 20.58 |
| Isoflurane | 35.28 ± 10.04* | 41.75 ± 10.92# |
| Recovery | 57.23 ± 17.41 | 78.94 ± 24.20*# |
| fEPSP Rate of rise (mv.ms⁻¹) | | |
| Control | 3.66 ± 1.60 | 5.42 ± 2.37 |
| Isoflurane | 2.49 ± 1.62# | 4.54 ± 2.20*# |
| Recovery | 3.72 ± 1.84 | 6.62 ± 2.20*# |

(*) Indicates statistical significance between vehicle and BAPTA-AM (#) indicates statistical significance between control and isoflurane effect or recovery under either vehicle or BAPTA-AM conditions.

P.S. Vehicle was DMSO 0.06% and BAPTA-AM concentration was 25 $\mu$M.

Figure 4:
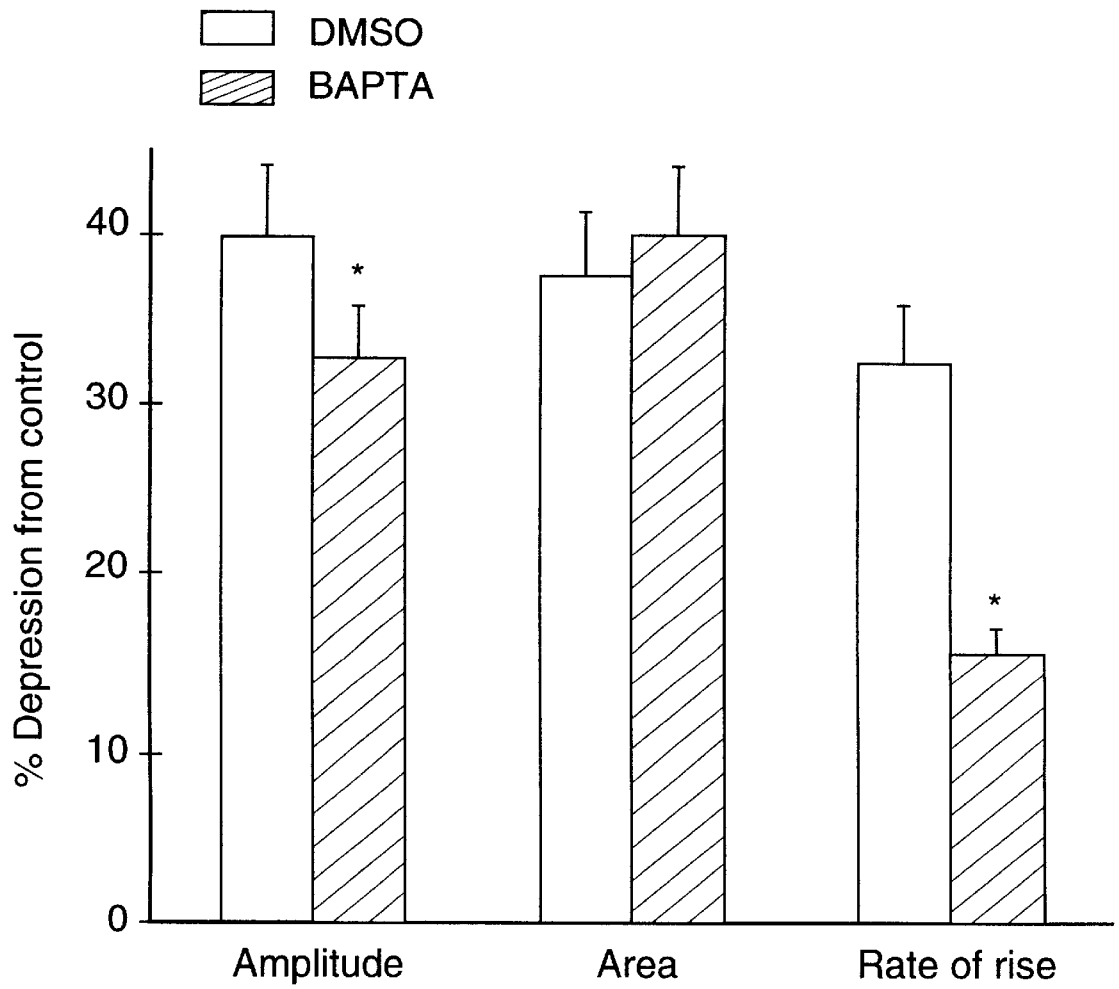
FIG. 4 represents a bar chart of percentage depression from a control of experiments on the effect of an anaesthetic on aged hippocampal slices.

The percent depression from control of the amplitude and rate of rise of recorded fEPSPs was less in slices incubated in BAPTA-AM compared to slices incubated in vehicle. The difference was statistically significant. FIG. 4 shows the effect of isoflurane (2%) on fEPSPs amplitude, area and rate of rise evoked in aged hippocampal slices treated with BAPTA-AM 25 $\mu$M and the vehicle DMSO 0.06%. (*) indicates statistical significance from DMSO ($p<0.05$, one-tailed paired t-test).

BAPTA-AM treatment of aged slices did not only oppose anaesthetic actions but also enhanced the recovery of the slices from isoflurane effects. For example, the percent increase of recovery fEPSPs from control, i.e. prior to anaesthetic application was much more pronounced in slices treated with BAPTA-AM compared to those incubated and perfused with the vehicle, (FIG. 5).

Figure 5:
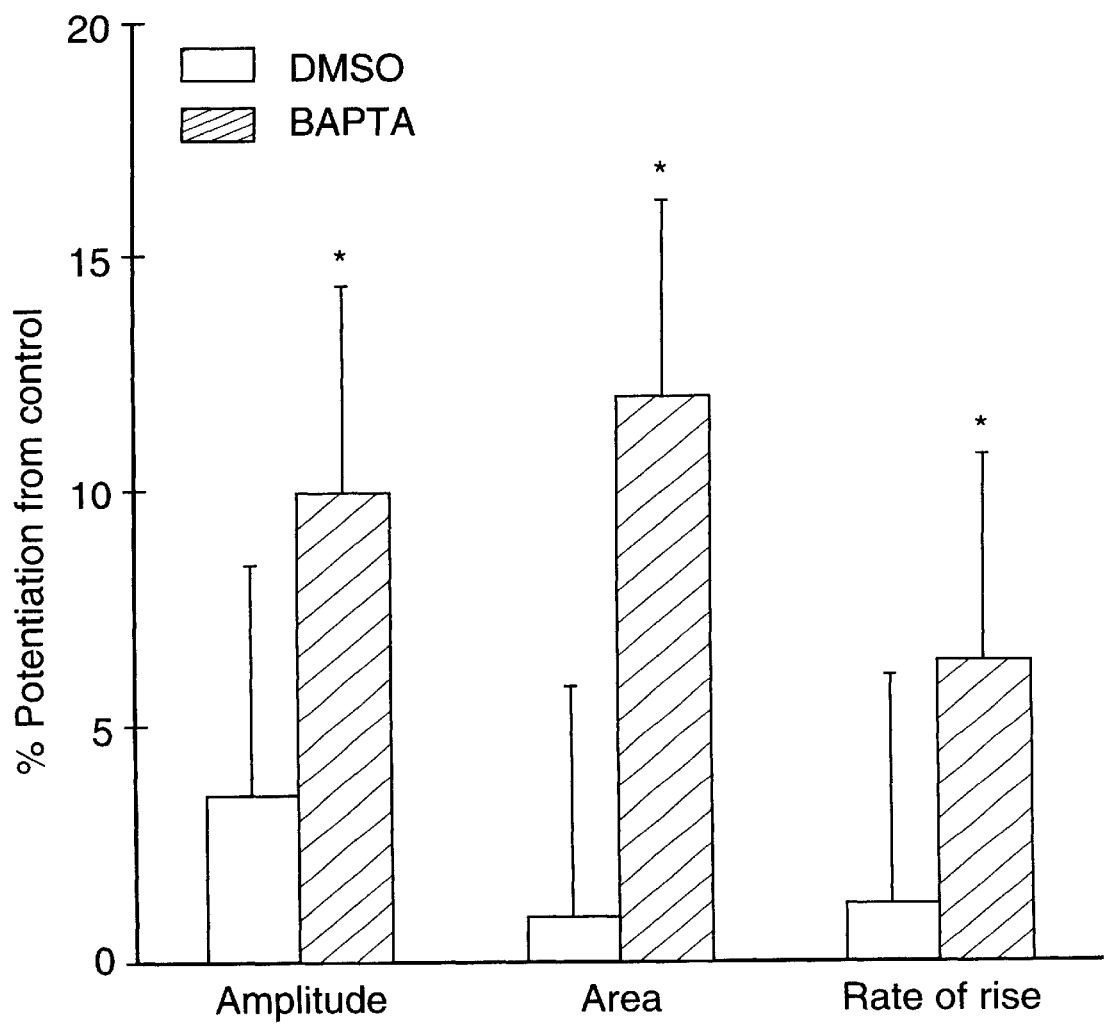
FIG. 5 represents a bar chart showing a rebound effect during recovery from an anaesthetic.

FIG. 5 shows fEPSP evoked in slices treated with BAPTA-AM (25 $\mu$M) demonstrated a rebound effect during recovery from isoflurane (2%). (*) Indicates statistical significance from DMSO ($p<0.05$, one-tailed paired t-test).

The effects of BAPTA-AM on anaesthetic actions in aged hipppocampal slices could be explained by the ability of the cell permeant BAPTA compound to chelate excess $[Ca^{2+}]_i$ that chronically accumulates during the advancement of age. Such buffering might increase the synaptic efficiency of the neurons. At presynaptic sites, decreasing pre-existing higher levels of $[Ca^{2+}]_i$ in aged neurons can increase neurotransmitter release probability. At the postsynaptic membrane, decrements in $[Ca^{2+}]_i$ will enhance voltage dependent $Ca^{2+}$ currents and increase intrinsic efficiency of postsynaptic receptors.

Figure 6:
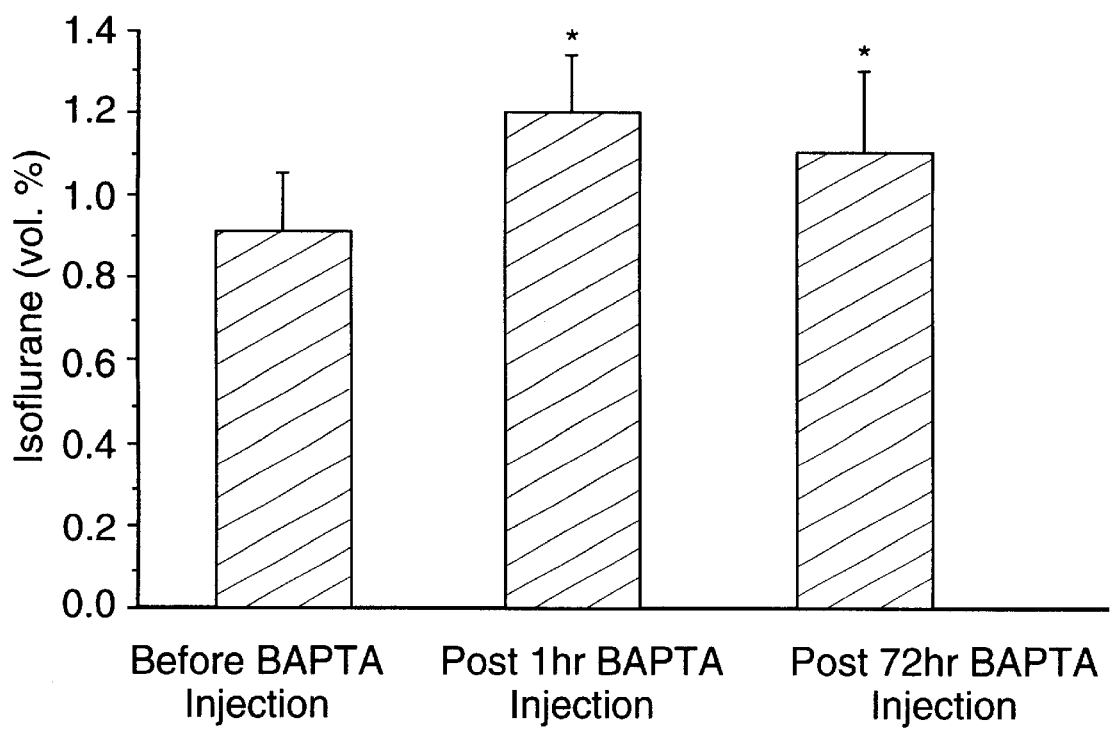
FIG. 6 represents a bar chart of the effect of a compound of use in the practice of the invention on the MAC of an anaesthetic.
Figure 7:
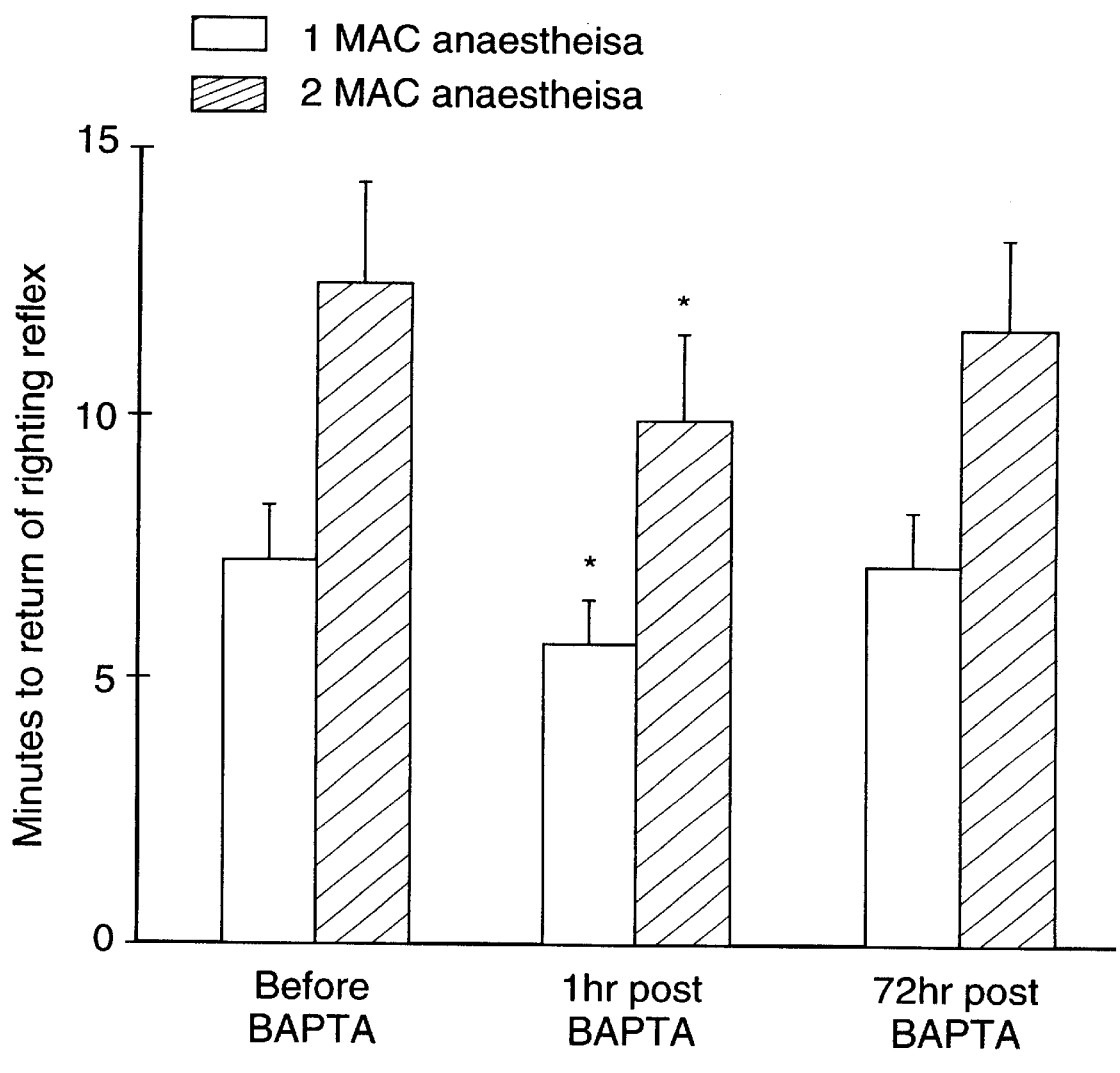
FIG. 7 represents a bar chart of the effect of a compound of use in the practice of the invention on recovery time after anaesthesia.

Phase II In Vivo Studies: Effects of BAPTA-AM Injection on Anaesthetic Requirements and Post-anaesthesia Recovery Time in Old Fisher 344 Rats A stirring feature in these investigations is that the MAC for isoflurane in old animals was increased by about 33% after BAPTA-AM injection. Such effect declined slightly after 72 hours of injection. FIG. 6 shows the effect of BAPTA-AM injection on the minimum alveolar concentration (MAC) of isoflurane determined in old Fisher 344 rats (n=5). (*) indicates statistical significance from "before BAPTA", ($p<0.05$, two-way ANOVA and Mann-Whitney U-test). The effect of BAPTA-AM treatment was consistent and showed small variability between animals. The design of repeated measures before and after treatment, ensured that each animal would act as its own control. The increase in MAC after treatment was statistically significant. The recovery time from isoflurane administration at two levels of anaesthesia was significantly less after BAPTA-AM injection. FIG. 7 shows the effect of BAPTA-AM injection in old Fisher 344 rats (n=5) on the recovery time of the righting reflex after isoflurane anaesthesia at 1 & 2 MAC. (*) indicates statistical significance from "before BAPTA" ($p<0.05$, two-way ANOVA and Mann-Whitney U-test). This effect did not persist after 72 hours of BAPTA-AM treatment.

Thus, the aforesaid results confirm that ageing-induced vulnerability to anaesthesia is partially antagonized by BAPTA-AM in in vitro and in in vivo administration to aged hippocampal slices and old Fisher 344 rats, respectively, to provide a therapeutic treatment for reversing ageing-potentiation of anaesthetic action.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

What is claimed is:

1. A method of alleviating impaired mental function and memory loss in aged mammals or reducing recovery time from anesthesia in aged mammals, said method comprising treating said mammal in need of said treatment with a non-toxic, effective amount of a cell membrane permeant calcium ion chelating buffer having a $K_D$ selected from the range of $1 \times 10^4$ to $1 \times 10^4$ calculated based on Molar amounts to increase neurotransmission in the brain in said aged mammal; and wherein said effective amount is sufficient to alleviate impaired mental function and memory loss or reduce recovery time from anesthesia in aged mammals.

2. The method as claimed in claim 1 wherein said cell membrane permeant calcium ion chelating buffer is essentially calcium ion-selective over other metal ions.

3. The method as claimed in claim 1 wherein said cell membrane permeant buffer is a compound having the formula:

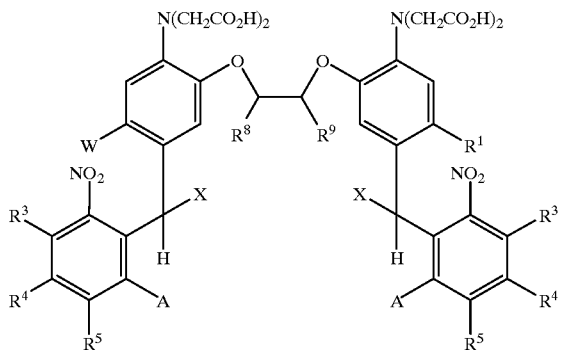

and the pharmaceutically acceptable nontoxic salts and esters thereof wherein:

A is —NO$_2$ or —H;

$R^1$ is selected from the group consisting of H, CH$_3$, F, Cl and Br;

$R^3$, $R^4$ and $R^5$ are independently H, OH, NR$^6$R$^7$, or alkoxy, or adjacent $R^3$ and $R^4$ together are —OCH$_2$O— or —OCH$_2$CH$_2$O — and $R^5$ is H, OH, NR$^6$R$^7$, or alkoxy, or $R^4$ and $R^5$ together are —OCH$_2$O— or —OCH$_2$CH$_2$O— and adjacent and $R^3$ is H, OH, NR$^6$R$^7$ or alkoxy; X is selected from the group consisting of OH, alkoxy, Cl, Br, NR$^6$R$^7$, OCOCH$_3$, OCOCF$_3$, OCOCH$_2$NH$_2$, OPO$_3$H, and OSO$_2$CH$_3$;

$R^6$ and $R^7$ are independently H, CH$_3$ or C$_2$H$_5$;

$R^8$ and $R^9$ are independently H, CH$_3$, C$_2$H$_5$, or CH$_2$OH, except that both may not be H simultaneously; or $R^8$ and $R^9$ together are —(CH$_2$)$_m$—Y—(CH$_2$)$_n$— where m and n are independently 1 or 2 and Y is selected from the group containing of —CH$_2$—, —O—, NR$^6$, —S—S—, and —S—S— and W is H, OH or NR$^6$.

4. The method as claimed in claim 1 wherein said cell membrane permeant buffer is a compound having the formula:

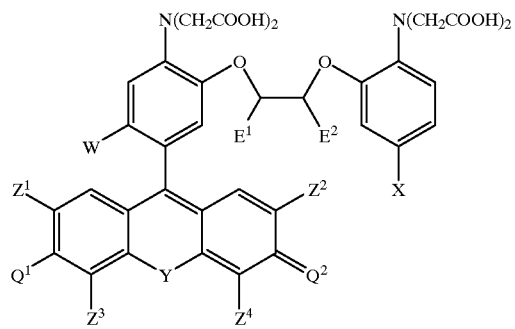

and the pharmaceutically acceptable non-toxic salts and esters thereof wherein:

A is NO$_2$ or H;

$R^1$ is selected from the group consisting of H unless $R^2$ is also H, CH$_3$, F, Cl, and Br;

$R^2$ is selected from the group consisting of H unless $R^1$ is also H, CH$_3$, F, Cl, Br, and C$_1$–C$_4$ alkoxy;

$R^3$, $R^4$ and $R^5$ are independently —H, OH, NR$^6$R$^7$, or alkoxy, or $R^3$ and $R^4$ together are —OCH$_2$O— or —OCH$_2$CH$_2$O— and $R^5$ is H, OH, NR$^6$R$^7$ or alkoxy, or $R^4$ and $R^5$ together are —OCH$_2$O— or —OCH$_2$CH$_2$O— and $R^3$ is H, OH, NR$^6$R$^7$or alkoxy;

X is selected from the group consisting of OH, alkoxy, Cl, Br, NR$^6$R$^7$, —OCOCH$_3$, —OCOCF$_3$, —OCOCH$_2$NH$_2$, —OPO$_3$H, and —OSO$_2$CH$_3$;

$R^6$ and $R^7$ are independently H, methyl or ethyl;

$R^8$ and $R^9$ are independently H, CH$_3$, C$_2$H$_5$, or CH$_2$OH except that both may not be H simultaneously; or $R^8$ and $R^9$ together are —(CH$_2$)$_m$—Y—(CH$_2$)$_n$— where m and n are independently 1 or 2 and Y is selected from the group consisting of —CH$_2$—, —O—, —NR$^6$, —S— and —S—S—; and W is H, OH, or NHR$^6$.

5. The method as claimed in claim 1, wherein said cell membrane permeant buffer is a compound having the formula:

and the pharmaceutically acceptable non-toxic salts and esters thereof wherein;

$E^1$ and $E^2$ are independently H, CH$_3$, C$_2$H$_5$, CH$_2$OH, COOH, or CH$_2$COOH or $E^1$ and $E^2$ together are —(CH$_2$)$_m$—V—(CH$_2$)$_n$— where m and n are independently 1 or 2 and V is selected from the group consisting of —(CH$_2$)—, —O—, —(NH)—, —(NMe)—, —S—, and —S—S—;

W is H, OH, or COOH;

X is H, Me, COOH, F, Cl, Br, I or $NO_2$;

Y is —O—, —(NMe)—, —S—, —($CH_2$)—, —($CMe_2$)—, —($CF_2$)—, or a direct sigma bond making a five-membered central ring;

$Z^1$, $Z^2$, $Z^3$ and $Z^4$ are independently H, F, Cl, Br, I, or Me;

$Q^1$ is $R_1R_2N$—, or H, where $R_1$ and $R_2$ are independently selected from the group consisting of H, Me and Et; and $Q^2$ is O.

6. The method as claimed in claim 1, wherein said cell membrane permeant buffer is a compound having the formula:

and the pharmaceutically acceptable non-toxic salts and esters thereof wherein;

$E^1$ and $E^2$ are independently H, $CH_3$, $C_2H_5$, $CH_2OH$, COOH, or $CH_2COOH$ or $E^1$ and $E^2$ together are —($CH_2$)$_m$—V—($CH_2$)$_n$— where m and n are independently 1 or 2 and V is selected from the group consisting of —($CH_2$)—, —O—, —(NH)—, —(NMe)—, —S—, and —S—S—;

W is H, OH, or COOH;

X is H, Me, COOH, F, Cl, Br, I or $NO_2$;

Y is —O—, —(NMe)—, —S—, —($CH_2$)—,—($CMe_2$)—, —($CF_2$)—, or a direct sigma bond making a five-membered central ring;

$Z^1$, $Z^2$, $Z^3$ and $Z^4$ are independently H, F, Cl, Br, I, or Me;

$Q^1$ is $R_1R_2N$—, or H, where $R_1$ and $R_2$ are independently selected from the group consisting of H, Me and Et; and $Q^2$ is O.

7. The method as claimed in claim 1 where in said cell membrane permeant buffer is a compound having the formula:

and the salts or the non-polymeric esters thereof wherein $R^1$ and $R^3$ are each independently selected from H, OH, $CH_3$, F, Cl, Br, I, COOH, CN, $NO_2$ or $NHR^7$ wherein $R^7$ is independently selected from H, methyl or ethyl;

$R^2$ is —(C=O)$CR^8$—N—N, wherein $R^8$ is independently selected from H, C1–C4 alkyl, phenyl, —COOH, —$COOR^7$, —(C=O)$CH_3$, or $CF_3$ wherein $R^7$ is H, $CH_3$ or $C_2H_3$;

$R^4$ is independently selected from $R^2$, H, $CH_3$, $CH_2CH_3$, F, Cl, Br, I, COOH, CN or $NO_2$;

$R^5$ and $R^6$ are each independently selected from H, $CH_3$, $CH_2CH_5$, phenyl, or $CH_2OH$, or $R^5$ and $R^6$ together form —($CH_2$)$_m$—Y—($CH_2$)$_n$— where m and n are each independently 1 or 2, and Y is selected from —$CH_2$—, —O—, —$NHR^7$, —S— or —S—S— S, and wherein $R^7$ is H, $CH_3$ or $C_2H_3$.

8. The method as claimed in claim 1 wherein said cell membrance permeant buffer is selected from the group consisting of BAPTA-AM; EGTA-AM; 5,5' dibromo BAPTA-AM; 5,5' difluoro BAPTA-AM; and 4,4'-difluoro BAPTA-AM.

9. The method as defined in claim 1 wherein said cell membrane permeant calcium buffer is administered to said mammal intravenously, intracathally, intracisternally, intraventricularly, topically, sub-cutaneously, by ingestion or by intramuscular injection.

10. The method as defined in claim 1 wherein said buffer is administered in the presence of a pharmaceutically acceptable anion transport inhibitor.

11. The method as defined in claim 10 wherein said anion transport inhibitor is probenecid.

12. The method as defined in claim 10 wherein said anion transport inhibitor is administered prior to administration of said calcium buffer.

* * * * *